United States Patent
Hidaka et al.

[11] Patent Number: 6,095,970
[45] Date of Patent: Aug. 1, 2000

[54] ENDOSCOPE

[75] Inventors: Tsuneo Hidaka; Teruo Ouchi, both of Saitama-Ken, Japan

[73] Assignee: Asahi Kogaku Kogyo Kabushiki Kaisha, Tokyo, Japan

[21] Appl. No.: 09/025,632

[22] Filed: Feb. 18, 1998

[30] Foreign Application Priority Data

| Feb. 19, 1997 | [JP] | Japan | 9-034182 |
| Feb. 19, 1997 | [JP] | Japan | 9-034183 |
| Feb. 19, 1997 | [JP] | Japan | 9-034184 |
| Feb. 19, 1997 | [JP] | Japan | 9-034185 |
| Feb. 19, 1997 | [JP] | Japan | 9-034186 |
| Feb. 19, 1997 | [JP] | Japan | 9-034187 |
| Feb. 19, 1997 | [JP] | Japan | 9-034188 |

[51] Int. Cl.$^7$ ...................................................... A61B 1/05
[52] U.S. Cl. ........................... 600/110; 600/109; 600/129; 600/172; 600/175
[58] Field of Search ...................... 600/109, 110, 600/112, 129, 130, 172, 175

[56] References Cited

U.S. PATENT DOCUMENTS

| 4,860,732 | 8/1989 | Hasegawa et al. | 600/109 |
| 4,895,138 | 1/1990 | Yabe . | |
| 4,918,521 | 4/1990 | Yabe et al. | 600/109 |
| 4,936,307 | 6/1990 | Saito et al. | 600/109 |
| 4,974,075 | 11/1990 | Nakajima | 600/110 |
| 4,998,182 | 3/1991 | Krauter et al. | 600/110 |
| 5,287,191 | 2/1994 | Suzuki et al. | 348/65 |
| 5,305,736 | 4/1994 | Ito . | |
| 5,325,847 | 7/1994 | Matsuno . | |
| 5,411,020 | 5/1995 | Ito . | |
| 5,427,087 | 6/1995 | Ito et al. . | |
| 5,454,366 | 10/1995 | Ito . | |
| 5,512,036 | 4/1996 | Tamburrino et al. | 600/172 |
| 5,547,457 | 8/1996 | Tsuyuki et al. . | |
| 5,609,561 | 3/1997 | Uehara et al. | 600/112 |
| 5,685,823 | 11/1997 | Ito et al. . | |
| 5,879,285 | 3/1999 | Ishii | 600/130 |

FOREIGN PATENT DOCUMENTS

| 0745347 | 12/1996 | European Pat. Off. . |
| 4-512212 | 2/1992 | Japan . |
| 8-24208 | 1/1996 | Japan . |
| 8201706 | 8/1996 | Japan . |

*Primary Examiner*—John Leubecker
*Attorney, Agent, or Firm*—Greenblum & Bernstein P.L.C.

[57] ABSTRACT

An endoscope includes a insertion tube which is inserted into a human body, an imaging device, an object optical system which forms image on the imaging device, a detachable unit accommodating the imaging device and the object optical system. The detachable unit is detachably mounted to a mounting portion of the insertion tube. At least one first contact is provided to the detachable unit. At least one second contact is provided to the mounting portion. The first and second contacts are electrically connected when the detachable unit is mounted to the mounting portion. A waterproof arrangement is provided to prevent water from entering a connecting potion of the first and second contacts.

41 Claims, 29 Drawing Sheets

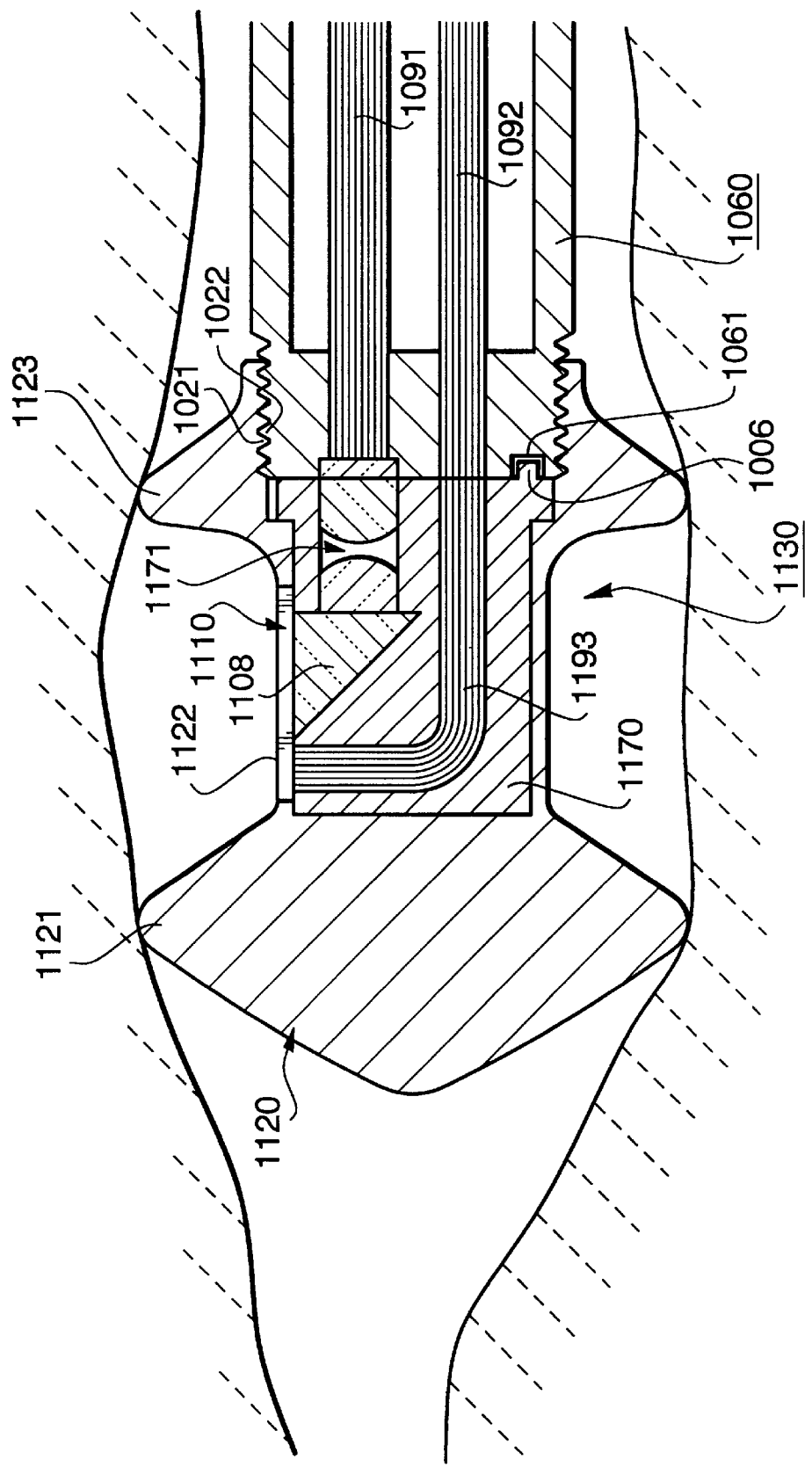

ENDOSCOPE

BACKGROUND OF THE INVENTION

The present invention relates to an endoscope.

In order to observe a human body cavity, a general endoscope has an object optical system and an imaging device. The object optical system and the imaging device are provided at a tip of an insertion tube of the endoscope. Generally, a charge-coupled device (hereinafter, referred to as a CCD) is used as the imaging device.

The endoscope must be sterilized every time the endoscope is used. Recently, an autoclaving method is widely use to sterilize the endoscope, since the autoclaving method is harmless to a human body and is capable of killing Helicobacter Pylori and viruses, etc. In the autoclaving method, a work is placed under a high-temperature (about 120° C. to 130° C.). However, since the CCD may break when heated more than 80° C., it is difficult to sterilize an endoscope with the CCD by autoclaving method.

Further, since the pitch between pixels of the CCD is small (almost 6 μm to 10 μm), the CCD may break when an electric discharge occurs in case the static electricity is generated during the assembly of the endoscope. Also, the CCD may break due to an impact when the tip of the endoscope is hit against something. In such cases, the endoscope must be totally disassembled and reassembled in order to replace the CCD.

Furthermore, a recently developed endoscope has a hood at the tip of an insertion tube. The hood is provided for urging a surface of a human body cavity thereby to keep an appropriate distance between an object (a surface of the human body cavity) and an optical system (accommodated in the insertion tube). The hood is fixed to the insertion tube. Thus, in case of replacing the CCD or the optical system of the insertion tube, it is necessary to remove the hood beforehand. This makes the replacing operation complicated.

SUMMARY OF THE INVENTION

It is therefore an object of the present invention to provide an endoscope wherein it is prevented that an imaging device thereof breaks due to the sterilization, and wherein it is easy to replace a broken imaging device.

According to one aspect of the present invention, there is provided an endoscope comprising a insertion tube which is inserted into a human body, an imaging device, an object optical system which forms image on the imaging device, a detachable unit accommodating the imaging device and the object optical system, and a mounting portion (provided to a tip of the insertion tube) to which the detachable unit is mounted. At least one first contact is provided to the detachable unit. At least one second contact is provided to mounting portion. The first and second contacts are electrically connected when the detachable unit is mounted to the mounting portion.

As constructed above, when the imaging devise is broken, it is possible to replace the imaging device without totally dismantling the insertion tube. Further, since the insertion tube and the detachable unit can be sterilized separately. It is possible to sterilize the insertion tube by autoclave method and to sterilize the detachable unit by chemical sterilization method or the like. Accordingly, it is prevented that an imaging device of the endoscope breaks due to the sterilization.

In a preferred embodiment, a waterproof arrangement is further provided to prevent water from entering into a connecting portion of the first and second contacts. With such an arrangement, the signal transmission of the imaging device and the insertion tube is ensured.

In a particular arrangement, the first and second surfaces respectively include end surfaces of the detachable unit and the mounting portion. The end surfaces mate with each other.

In another arrangement, the detachable unit further includes a protrusion, while mounting portion further includes a recess that receives the protrusion. The first contact is provided to the protrusion, and the second contact is provided to the recess. Alternatively, mounting portion further includes a protrusion, while the detachable unit further includes a recess that receives the protrusion. The first contact is provided to the recess, and the second contact is provided to the protrusion.

In a further arrangement, the detachable unit has a fitting part, while the mounting portion has a receiving part that receives the fitting part. The first contact is provided to the fitting part, and the second contact is provided to the receiving part. In a yet further arrangement, the detachable unit has a first engaging member, while mounting portion has a second engaging member. The first and second engaging members constitute an bayonet mechanism.

It is another object of the present invention to provide an endoscope wherein an optical system can be easily replaced.

According to another aspect of the present invention, there is provided an endoscope including an object optical system, an insertion tube that supports a fiber bundle for sending image formed by the object optical system, an adapter body accommodating at least a part of the optical system, a hood provided around the adapter body, and a mounting portion (provided to a tip of the insertion tube) to which the hood is detachably mounted. The adapter body is detachably mounted to the mounting portion by mounting the hood to the mounting portion.

With such an arrangement, it is possible to replace the optical system (provided in the adapter body) only by disengaging the hood from the tip of the insertion tube. Thus, the replacement of the optical system becomes easy.

BRIEF DESCRIPTION OF THE DRAWINGS

FIG. 32 is a sectional view of another detachable unit and a mounting portion of the tenth embodiment.

DESCRIPTION OF THE PREFERRED EMBODIMENT

The first embodiment of the present invention is described.

Figure 1:
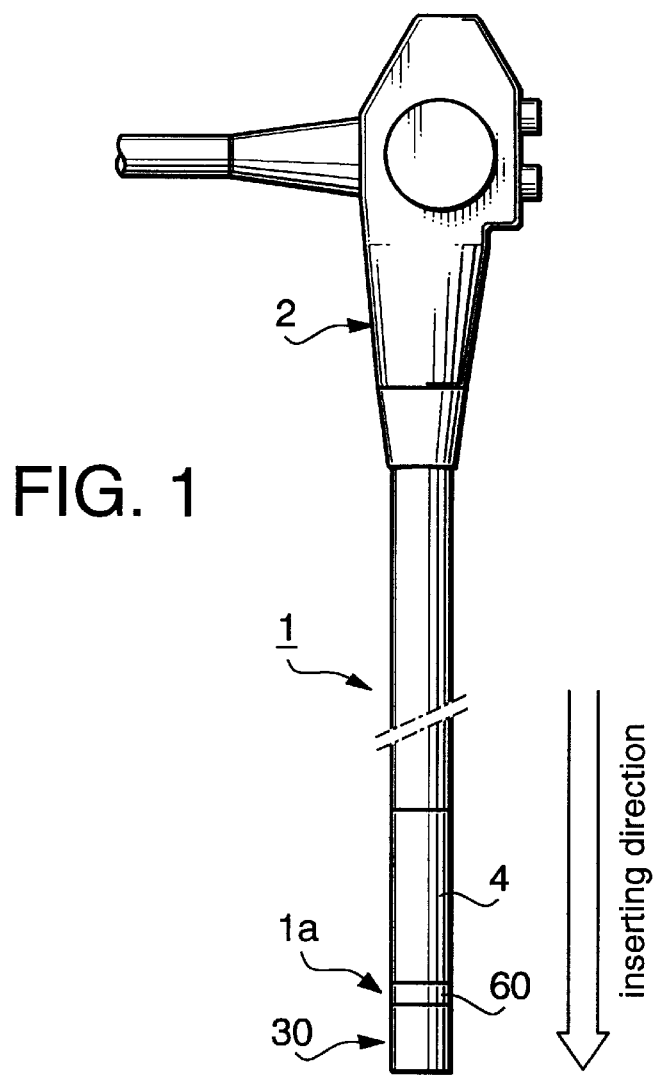
FIG. 1 is a plan view of an endoscope.

FIG. 1 shows an electronic endoscope of the first embodiment. The endoscope includes an insertion tube 1 which is to be inserted into a human body cavity. A manipulator 2 is provided to one end of the insertion tube 1, for operating not-shown medical instruments provided in the insertion tube 1. The manipulator 2 is connected to a not-shown controller unit (including a light source, water feeding device of the like). The insertion tube 1 includes a bending portion which can be bent freely by the remote manipulation by the manipulator 2. A detachable unit 30 is detachably mounted to the tip 1a of the insertion tube 1. The insertion tube 1 includes a mounting portion 60 at the tip 1a of the insertion tube 1, for mounting the detachable unit 30.

Figure 2:
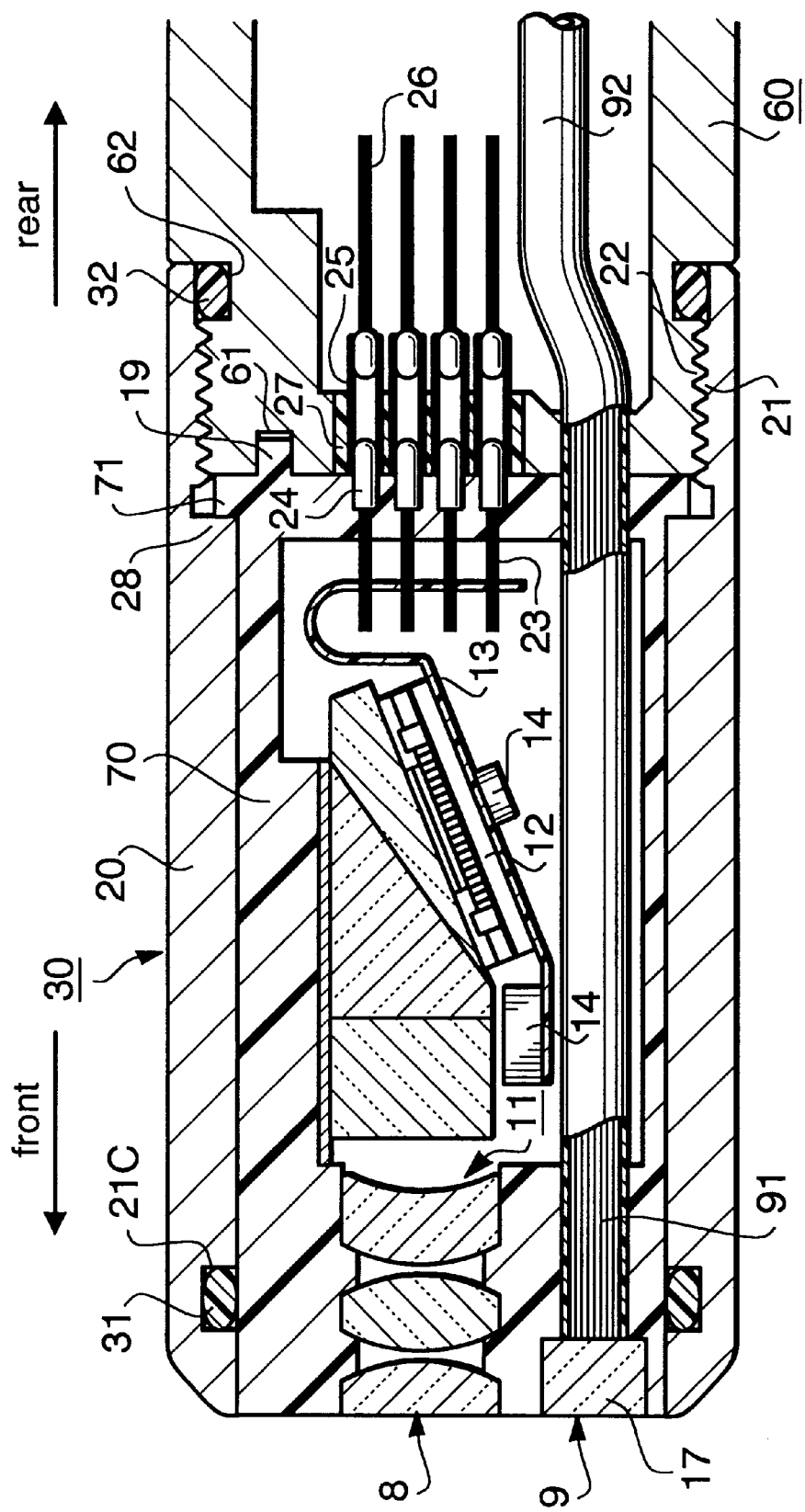
FIG. 2 is a sectional view of a detachable unit and a mounting portion of the first embodiment.

FIG. 2 is a sectional view of the detachable unit 30 and the mounting portion 60 of the insertion tube 1. The detachable unit 30 includes a cylindrical unit body 70, made of an insulating plastic. In order to observe the surface of the human body cavity, an object optical system 11 is provided in the unit body 70. The object optical system 11 is covered by a view window 8 disposed at the front end of the unit body 70. A CCD (charge-coupled device) 12 is provided at a portion where image is formed by the object optical system 11. The CCD 12 and electronic components 14 for driving the CCD 12 are mounted on a circuit board 13. Hereinafter, the direction in which the insertion tube 1 is inserted is referred to as 'front', and the opposite direction is referred to as 'rear'.

The unit body 70 can be attached to and detached from the mounting portion 60 of the insertion tube 1. The unit body 70 is provided with a projection 19 at the rear end face thereof, which fits indentation 61 formed on the front end face of the mounting portion 60. The position of the detachable unit 30 with respect to the mounting portion 60 is determined by the engagement between the projection 19 and the indentation 61.

A cylindrical hood 20 is provided around the unit body 70. The hood 20 is rotatable and slidable (in the direction of an axis of the unit body 70) on the unit body 70. The hood 20 has an internal thread 21, and the mounting portion 60 has an external thread 22. The hood 20 is fixed to the mounting portion 60 by the engagement of the external thread 22 and the internal thread 21. Thus, the unit body 70 is held between the mounting portion 60 and the hood 20. The axis of the unit body 70 is aligned with the axis of the mounting portion 60 of the insertion tube 1.

In order to electrically connect the detachable unit 30 and the mounting portion 60, first contacts 24 are provided at the rear end face of the unit body 70. The first contacts 24 are connected to a circuit (not shown) provided on the circuit board 13 via wires 23. The first contacts 24 are pin-shaped and protruded rearward in the direction parallel to the axial direction of unit body 70. Second contact 25 are provided to the front end face of mounting portion 60. The second contacts 25 are tubular-shaped and are extended in the direction parallel to the axial direction of mounting portion 60. The second contacts 25 are supported by an insulating member 27 and are connected to wires 26 provided in the mounting portion 60.

Figure 3:
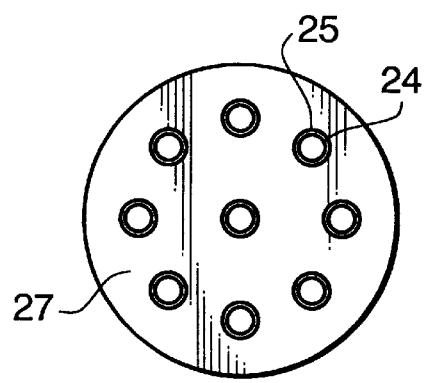
FIG. 3 is a schematic view showing an example of an arrangement of contacts.

FIG. 3 shows the example of the arrangement of the first and second contacts 24 and 25, seen from the front thereof. In this example, the first and second contacts 24 and 25 are arranged in a circumference, so that a lot of contacts can be provided in a relatively small area.

With such an arrangement, when the detachable unit 30 is mounted to the mounting portion 60 of the insertion tube 1, the first contacts 24 fit into the second contacts 25 (in the direction of the axis of unit body 70 and the axis of the mounting portion 60). Thus, the first and second contacts 24 and 25 are electrically connected, so that signals (for example, image signals outputted by the CCD 12) are thereby transmitted between the CCD 12 and the wire 26 in the insertion tube 1.

The mounting operation of the detachable unit 30 to the mounting portion 60 is described. Prior to the mounting of the detachable unit 30, the hood 20 is moved beforehand so that the hood 20 is protruded from the front end of the unit body 70. Then, the unit body 70 is attached to the mounting portion 60 so that the projection 19 engages the indentation 61 and so that the first and second contacts 24 and 25 fit with each other. In this state, the relative position of the first contacts 24 with respect to the mounting portion 60 is determined by the engagement of the projection 19 and the indentation 61 and the fitting of the first and second contacts 24 and 25. After the unit body 70 is mounted to the mounting portion 60, the hood 20 is moved toward the mounting portion 60 so that the internal thread 21 of the hood 20 engages the external thread 22 of the mounting portion 60. A shoulder portion 28 is formed on the inner surface of the hood 20. A flange portion 71 is formed on the circumference of the unit body 70. When the internal thread 21 of the hood 20 engages the external thread 22 of the mounting portion 60, the shoulder portion 28 of the hood 20 abuts the flange portion 71 of the unit body 70. With this, the unit body 70 is fixed to the mounting portion 60 so that the unit body 70 is urged onto the front surface of the mounting portion 60. When the detachable unit 30 is mounted to the mounting portion 60, the front end of the hood 20 and the front end of the unit body 70 are aligned on a same plane. On removing the hood 20 from the mounting portion 60, the hood 20 is rotated so as to release the engagement of the internal thread 21 and the external thread 22. Then, the hood 20 can be moved out of the mounting portion 60, with the first and second contacts 24 and 25 being disconnected.

In order to illuminate the human body cavity, a first fiber bundle 91 is provided in the detachable unit 30. The exit end of the first fiber bundle 91 is covered by an illumination window 9. The illumination window 9 includes a transparent glass cover 17. A second fiber bundle 92 is provided in the insertion tube 1 so that the exit end thereof is fixed to the mounting portion 60. The exit end face of the second fiber bundle 92 is in face-to-face contact with the rear end face of the first fiber bundle 91, when the detachable unit 30 is mounted to the mounting portion 60. Thus, illumination light is carried through the first and second fiber bundles 91 and 92.

A first O-ring 31 is provided to a peripheral groove 21c formed on the inner surface of the front portion of the hood 20 so that the first O-ring 31 contacts the outer surface of the unit body 70. A second O-ring 32 is provided to a peripheral groove 62 formed on a rear side of the external thread 22 of the mounting portion 60. This sealing arrangement prevents water intrusion through a gap between the hood 20 and the unit body 70 and a gap between the hood 20 and the mounting portion 60. Accordingly, it is prevented that the first and second contacts 24 and 25 get wet. That is, the faulty signal transmission is prevented.

Since the unit body 70 is made of plastic, the first contacts 24, the view window 8 and the illumination window 9 can be tightly fixed to the unit body 70. Further, since the insulating member 27 and a sheath of the second fiber bundle 92 can be tightly fixed to the mounting portion 60. That is, the unit body 70 and the mounting portion 60 have waterproof structures.

As constructed above, after removing the detachable unit 30 from the insertion tube 1, it is possible to sterilize the detachable unit 30 and the insertion tube 1 separately. Accordingly, the detachable unit 30 can be sterilized by the chemical sterilizing method, while the insertion tube 1 is sterilized by the autoclave method. With this, the CCD 12 does not suffer high temperature. Thus, it is prevented that the CCD 12 breaks because of the heat caused by the autoclave. Further, in case where the detachable unit 30 breaks, it is possible to replace the detachable unit 30 without totally disassembling the insertion tube 1.

Figure 4:
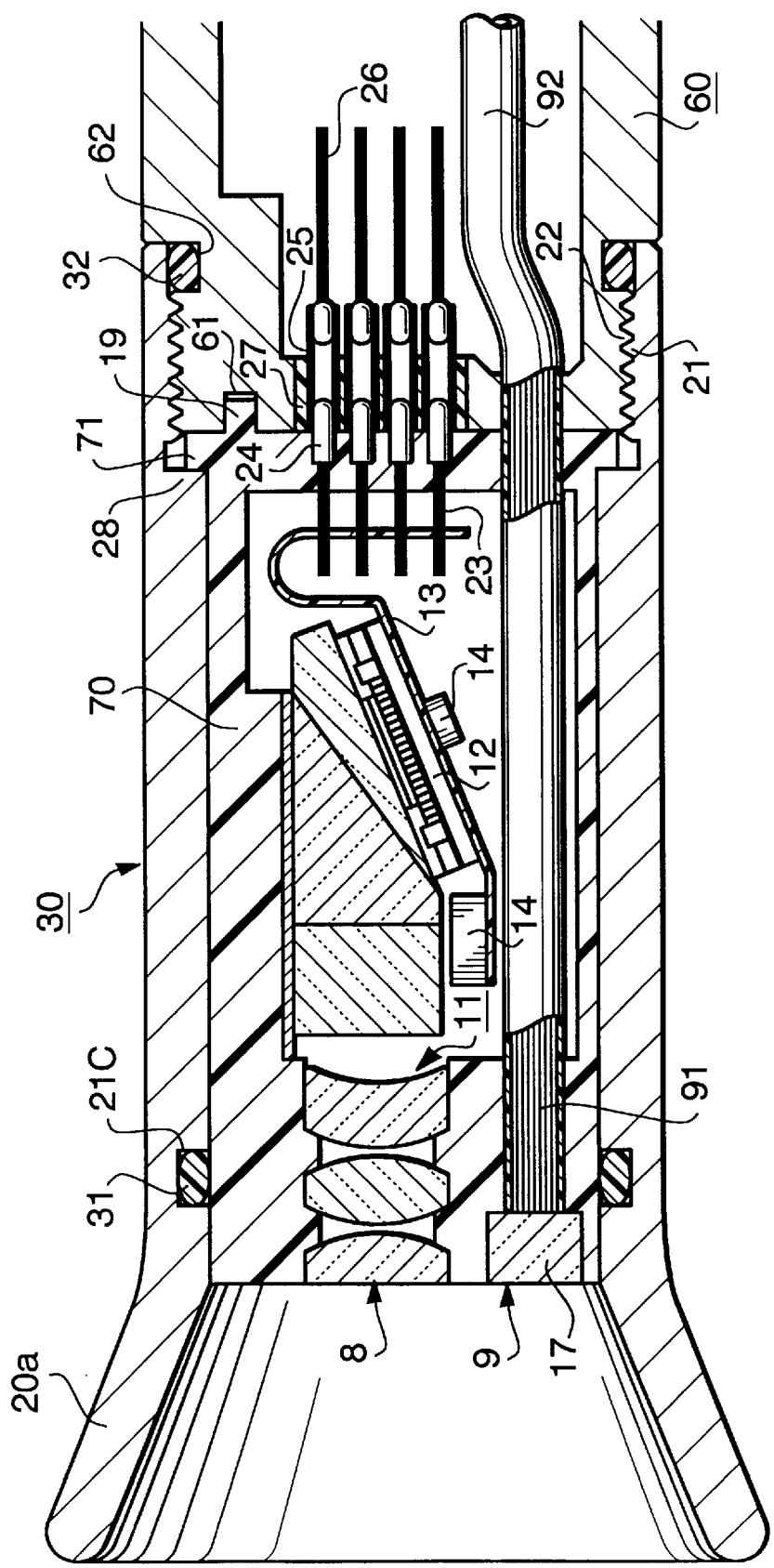
FIG. 4 is a sectional view showing a modification of the first embodiment.

FIG. 4 shows a modification of the first embodiment. In this modification, the front end portion of the hood 20a has bell-mouth-shape and is protruded frontward from a unit body 70. With this, it is possible to push a sticky surface of a human body cavity away from the detachable unit 30, thereby to keep an appropriate distance between the surface and the object optical system 11.

Figure 5:
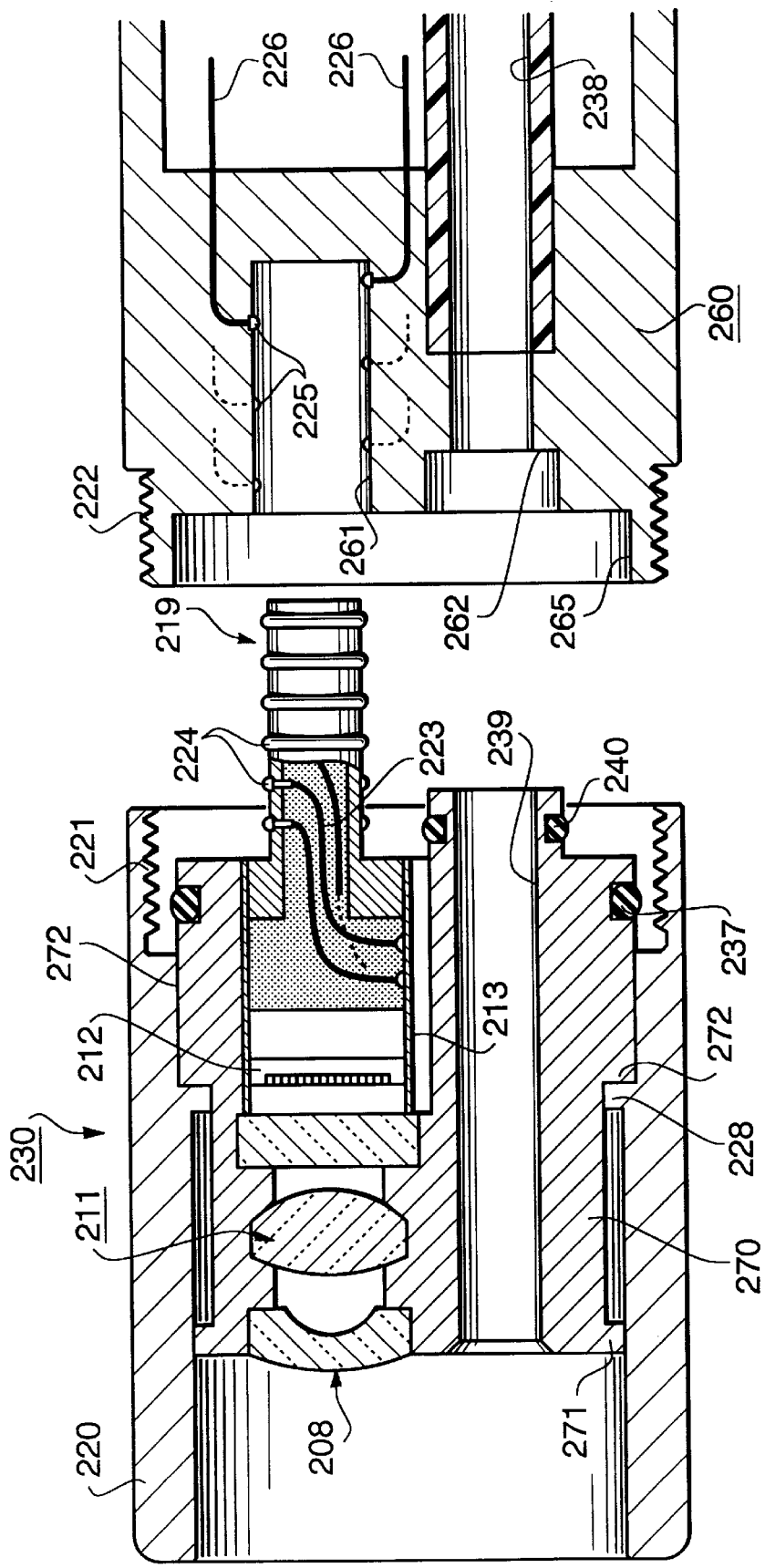
FIG. 5 is an exploded sectional view of a detachable unit and a mounting portion of the second embodiment.
Figure 6:
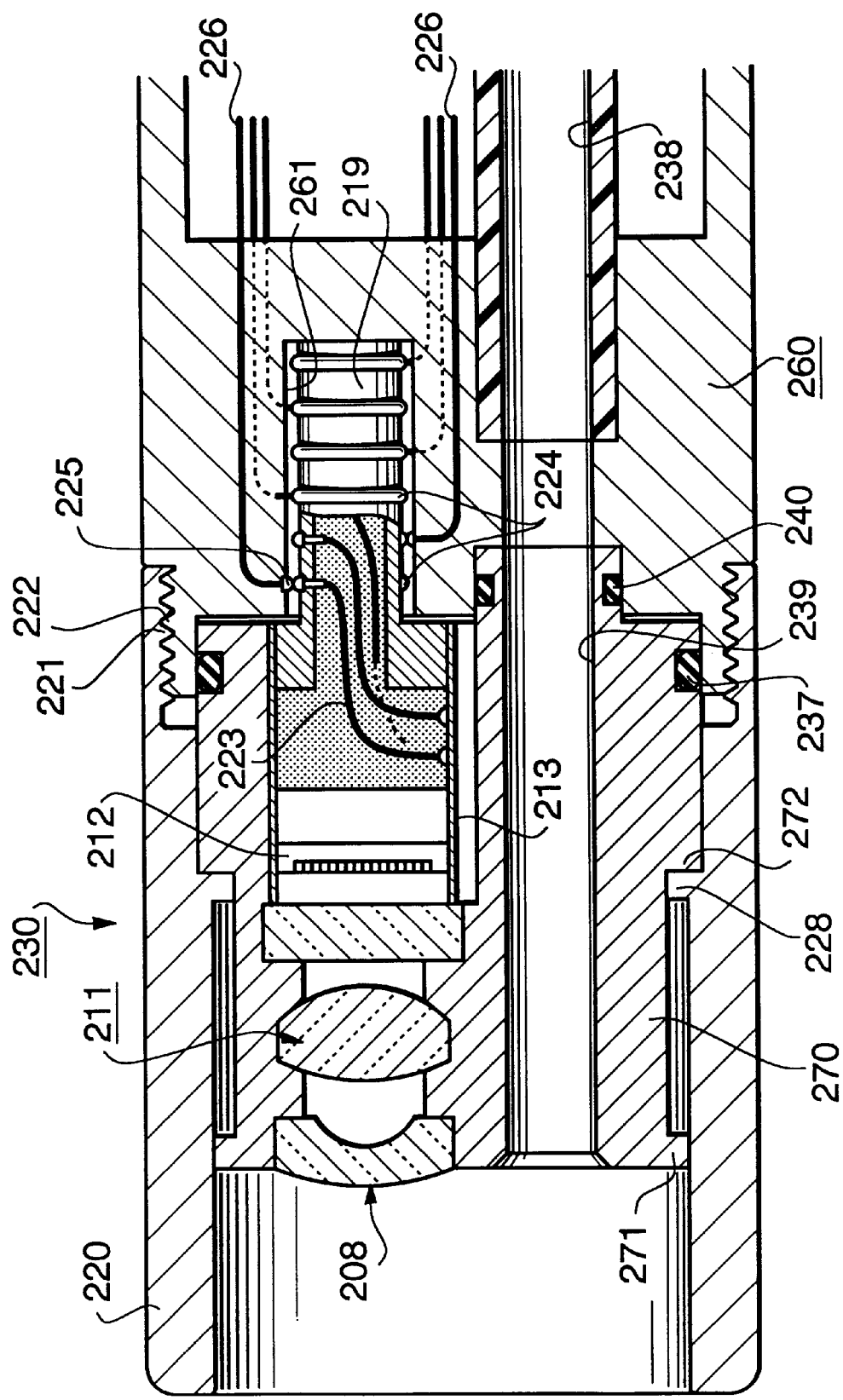
FIG. 6 is a sectional view of a detachable unit and a mounting portion of the second embodiment.

The second embodiment of the present invention is described. FIGS. 5 and 6 are an exploded sectional view and a sectional view of a detachable unit and a mounting portion of the second embodiment. As shown in FIG. 5, a detachable unit 230 of the second embodiment includes a cylindrical unit body 270 and a cylindrical hood 220. The unit body 270 accommodates an object optical system 211 and a CCD 212. The object optical system 211 is covered by a view window 208 disposed at the front end of the unit body 270. The object optical system 211 and the CCD 212 respectively have the same functions as the object optical system 11 and the CCD 12 of the first embodiment. The hood 220 is rotatable and slidable (in the direction of an axis of the unit body 270) on the unit body 270.

A mounting portion 260 of the second embodiment has a recess 265 to which a rear part of the unit body 270 fits. The hood 220 has an inner flange 228 formed on the inner surface thereof. The unit body 270 has front and rear outer flanges 271 and 272. When the hood 220 moves frontward, the inner flange 228 of the hood 220 abuts the front outer flange 271. When the hood 220 moves rearward, the inner flange 228 abuts the rear outer flange 272. Thus, the large diameter portions 271 and 272 restrict the moving range of the hood 220. When the hood 220 moves, the inner surface of the hood 220 slides along the circumference of the rear outer flange 272. The hood 220 has an internal thread 221 and the mounting portion 260 has an external thread 222. When the hood 220 is fixed to the mounting portion 260 as shown in FIG. 6, the rear large diameter portion of the unit body 270 is urged by the inner flange 228 of the hood 220. Thus, the unit body 270 is sandwiched between the hood 220 and the mounting portion 260 and held therebetween.

A cylindrical protrusion 219 is protruded rearward from the unit body 270. Ring-shaped first contacts 224 are formed on the outer surface of the cylindrical protrusion 219, each first contact 224 extending along the circumference of the cylindrical protrusion 219. The first contacts 224 are connected to the circuit board 213 provided in the unit body 270 (via wires 223). The cylindrical protrusion 219 fits into a hole 261 formed on the mounting portion 260, when the detachable unit 230 is mounted to the mounting portion 260. Second contacts 225 are formed on the inner surface of the hole 261, so that the second contacts 225 are in contact with the first contacts 224 when the protrusion 219 fit into the hole 261. The second contacts 225 are connected to wires 26 provided in the insertion tube 1. Thus, when the detachable unit 230 is mounted to the mounting portion 260, the first and second contacts 224 and 225 are electrically connected with each other. Further, since the protrusion 219 is not positioned on the axis of the unit body 270, the relative rotational movement of he unit body 270 with respect to the mounting portion 260 is restricted by the fitting of the protrusion 219 and the hole 261.

An O-ring 237 is provided to the outer surface of the unit body 270. The O-ring 237 abuts the inner surface of the hood 220 thereby to close the clearance between the unit body 270 and the recess 265. Thus, the first and second contacts 224 and 225 do not get wet when the detachable unit 230 is mounted to the mounting portion 260.

In order to introduce a medical instrument into a human body cavity, a first channel 239 is provided to the unit body 270. A second channel 238 is provided in the insertion tube, so that the front end thereof is fixed to the mounting portion 260. The mounting portion 260 is provided with a shoulder portion 262 formed at the exit opening of the second channel 238. When the detachable unit 230 is mounted to the mounting portion 260, the shoulder portion 262 receives the rear end of the first channel 239, so that the first and second channels 239 and 238 are aligned with each other. Thus, a medical instrument (such as forceps) can be introduced through the second channel 238 and the first channel 239. An O-ring 240 is provided to a outer circumference of the first channel 239 so that the O-ring 240 seals the clearance between the shoulder portion 262 and the first channel 239.

The axial length of the hood 220 is larger than that of the unit body 270, so that the hood 220 is protruded from the front end of the unit body 270. Such structure is suitable for inspecting an esophagus or a large intestine, since the hood 220 urges a sticky surface of a human body cavity away from the detachable unit 230, thereby to keep an appropriate distance between the surface and the object optical system.

The mounting operation of the detachable unit 230 to the mounting portion 260 is described. Before mounting the detachable unit, the hood 20 is moved frontward so that the inner flange 228 abuts the front outer flange 271. Then, the detachable unit 230 is moved toward the mounting portion 260 so that the protrusion 219 fits into the hole 261 of the mounting portion 260. Next, the hood 220 is rotated so that the internal thread 221 engages the external thread 222 of the mounting portion 260.

As constructed above, the detachable unit 230 can be easily replaced, without totally disassembling the insertion tube. Further, since the detachable unit 230 and the insertion tube can be separately sterilized after removing the detachable unit 230 from the insertion tube, it is prevented that the CCD 212 breaks because of the heat caused by the autoclave.

Figure 7:
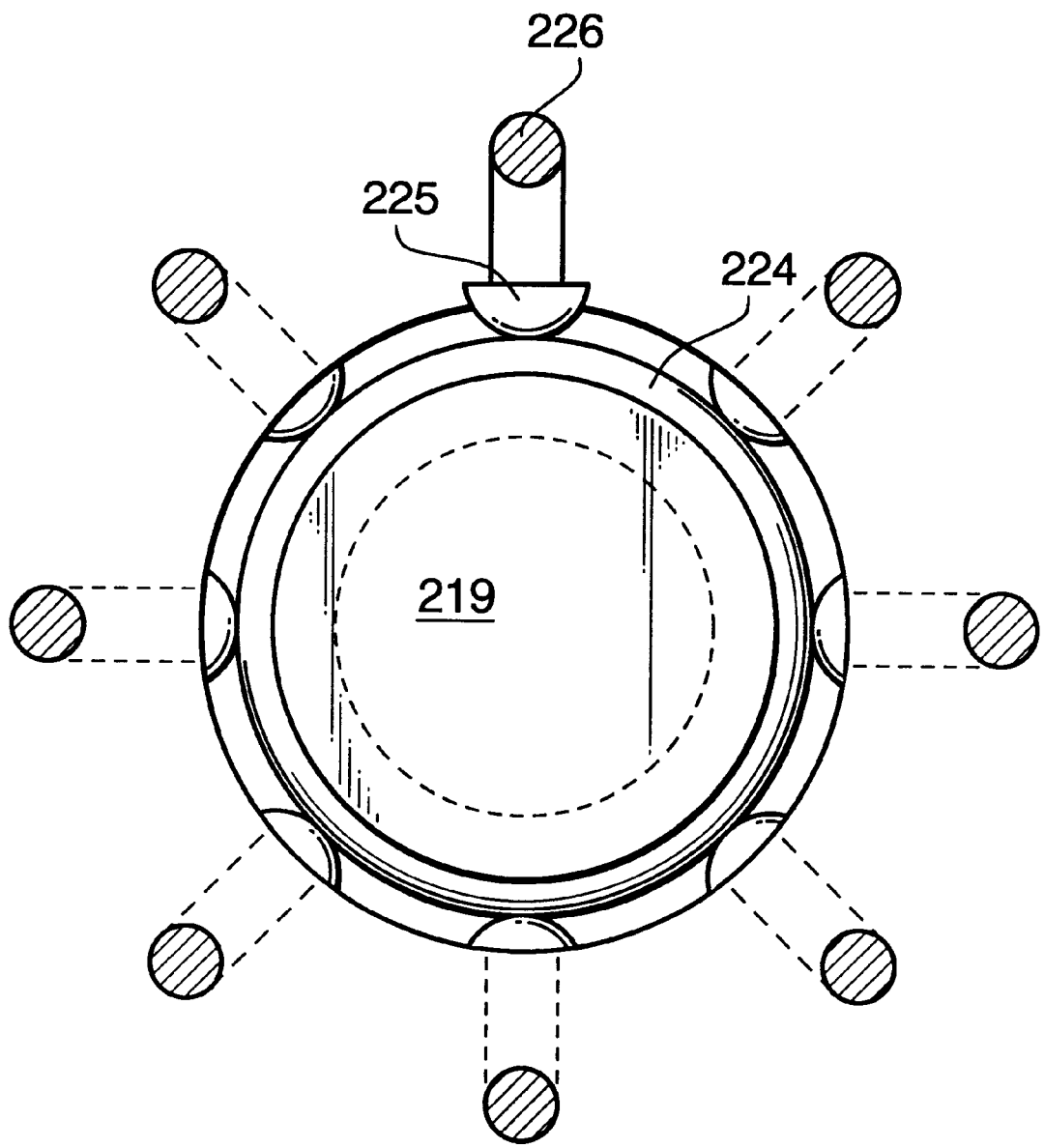
FIG. 7 is a schematic view showing an example of an arrangement of contacts.

FIG. 7 shows an example of the arrangement of the second contacts 225. It is possible to arrange the second contacts 225 on a circumference around the protrusion 219, while the first contacts 224 are arranged along the longitudinal direction of the protrusion 219 (as shown in FIG. 5).

Figure 8:
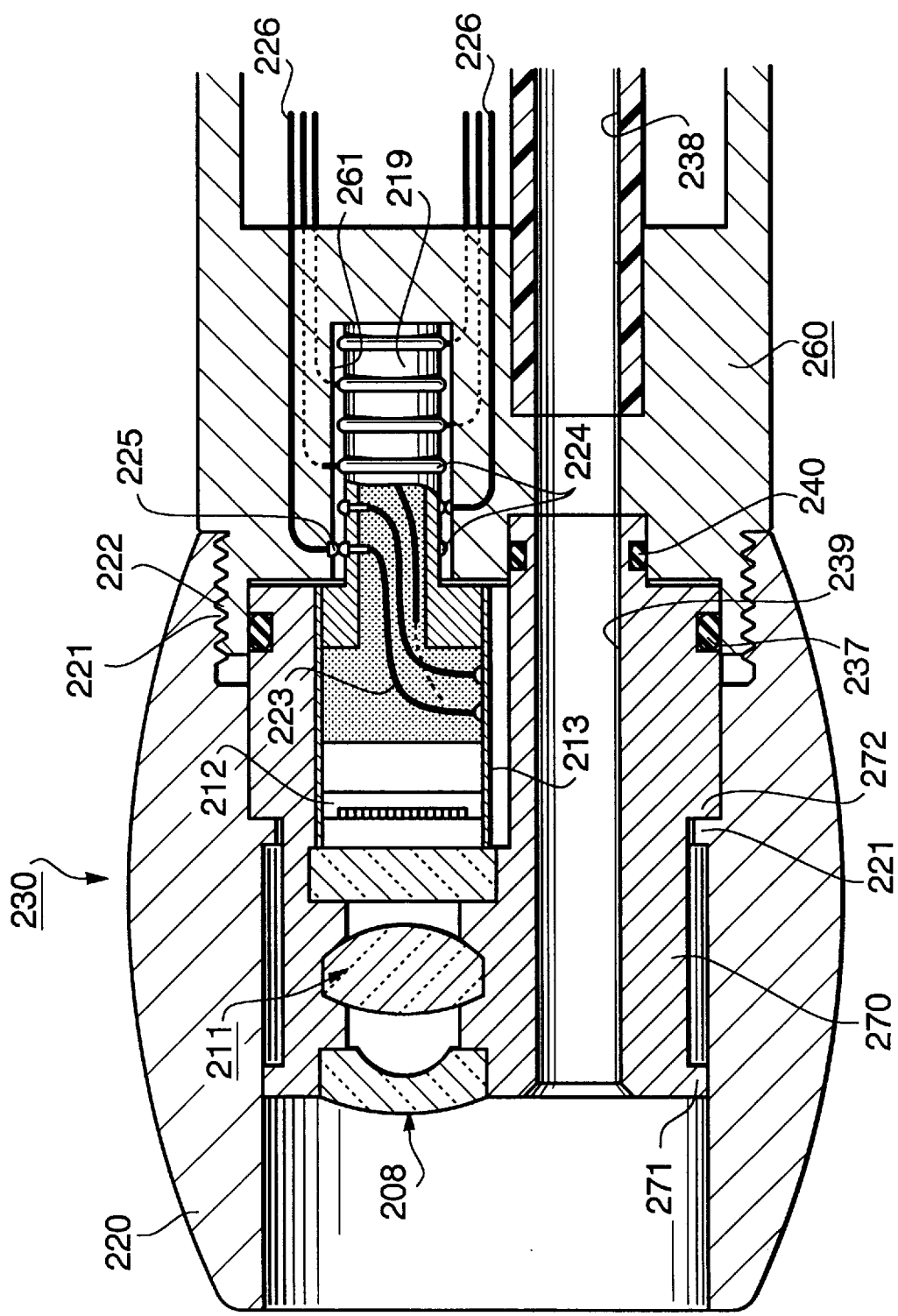
FIG. 8 is a sectional view showing a modification of the second embodiment.

FIG. 8 shows a modification of the second embodiment. In this modification, the front end portion of the hood 220 is round-shaped and is protruded from a front end of the unit body 270. With this, it is easy to insert the insertion tube into the human body cavity.

Figure 9:
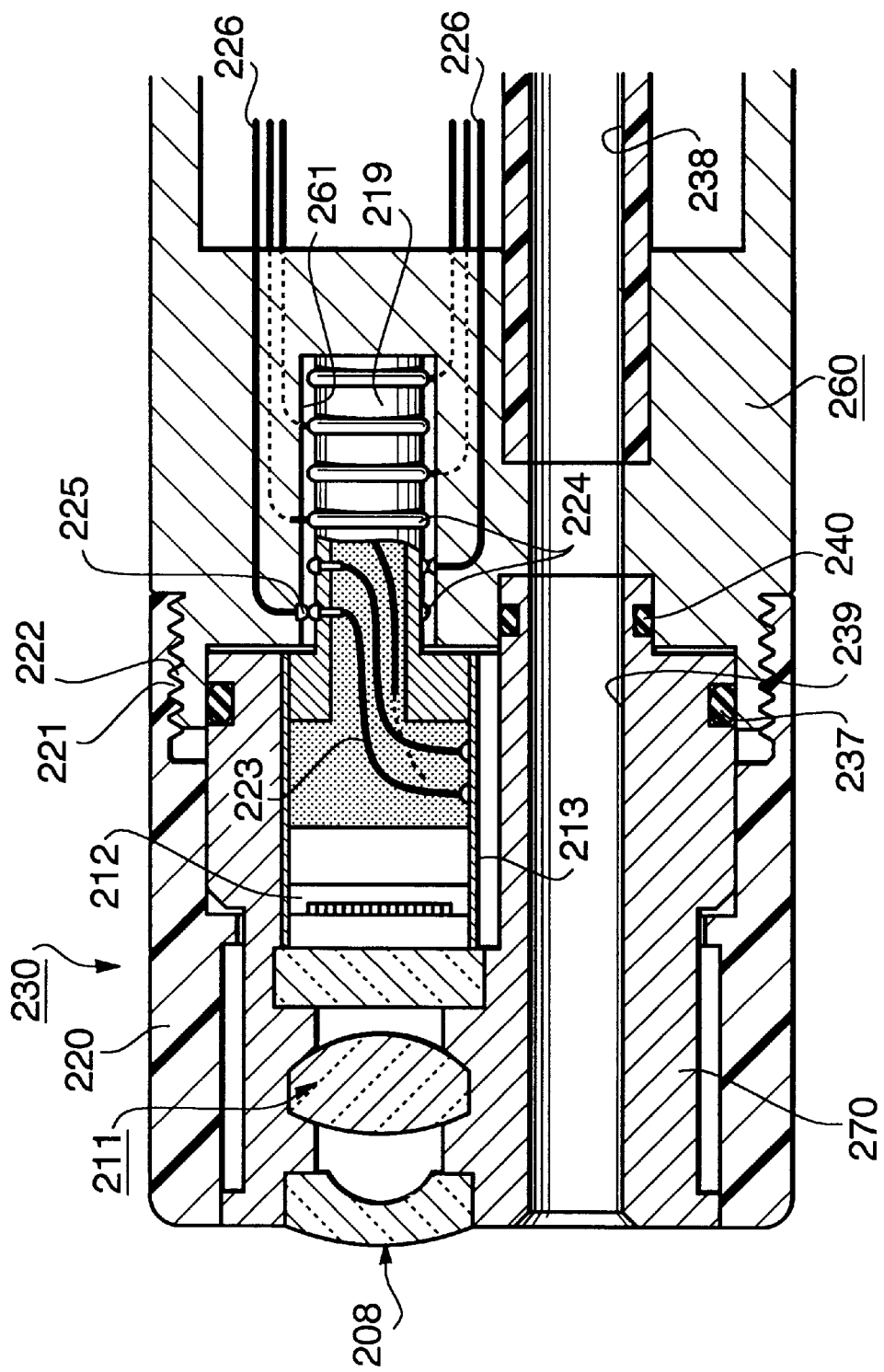
FIG. 9 is a sectional view showing another modification of the second embodiment.

FIG. 9 shows another modification of the second embodiment. In this modification, the hood 220 is made of plastic such as tetrafluoroethylene or Derlin. Further, the front end of the hood 220 and the front end of the unit body 270 are aligned on a same plane. Since the hood 220 is made of plastic, the object optical system 211 and the CCD 212 are protected by a shock applied to the detachable unit 230 (when the detachable unit 230 is hit against something).

Figure 10:
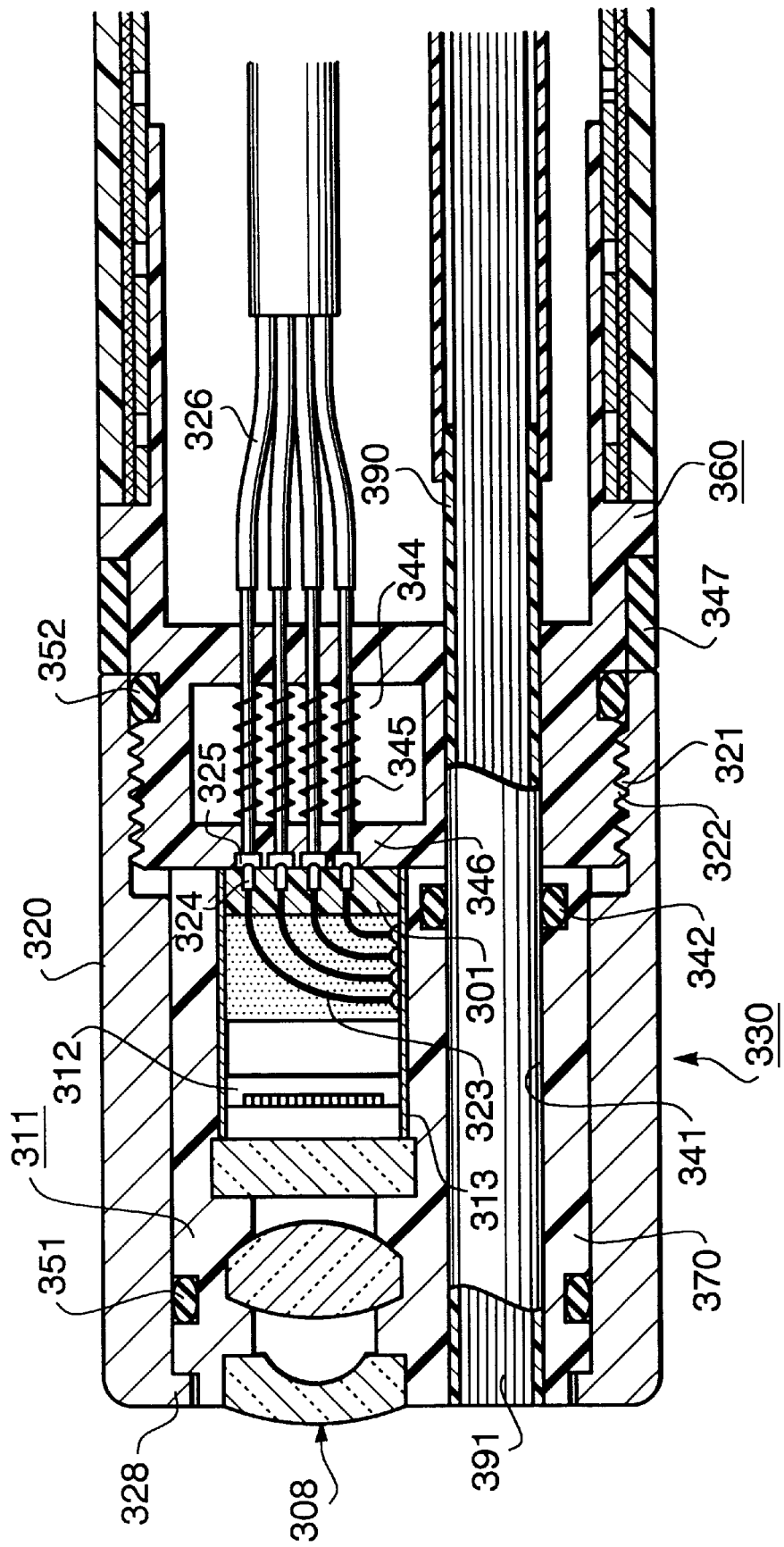
FIG. 10 is a sectional view of a detachable unit and a mounting portion of the third embodiment.
Figure 11:
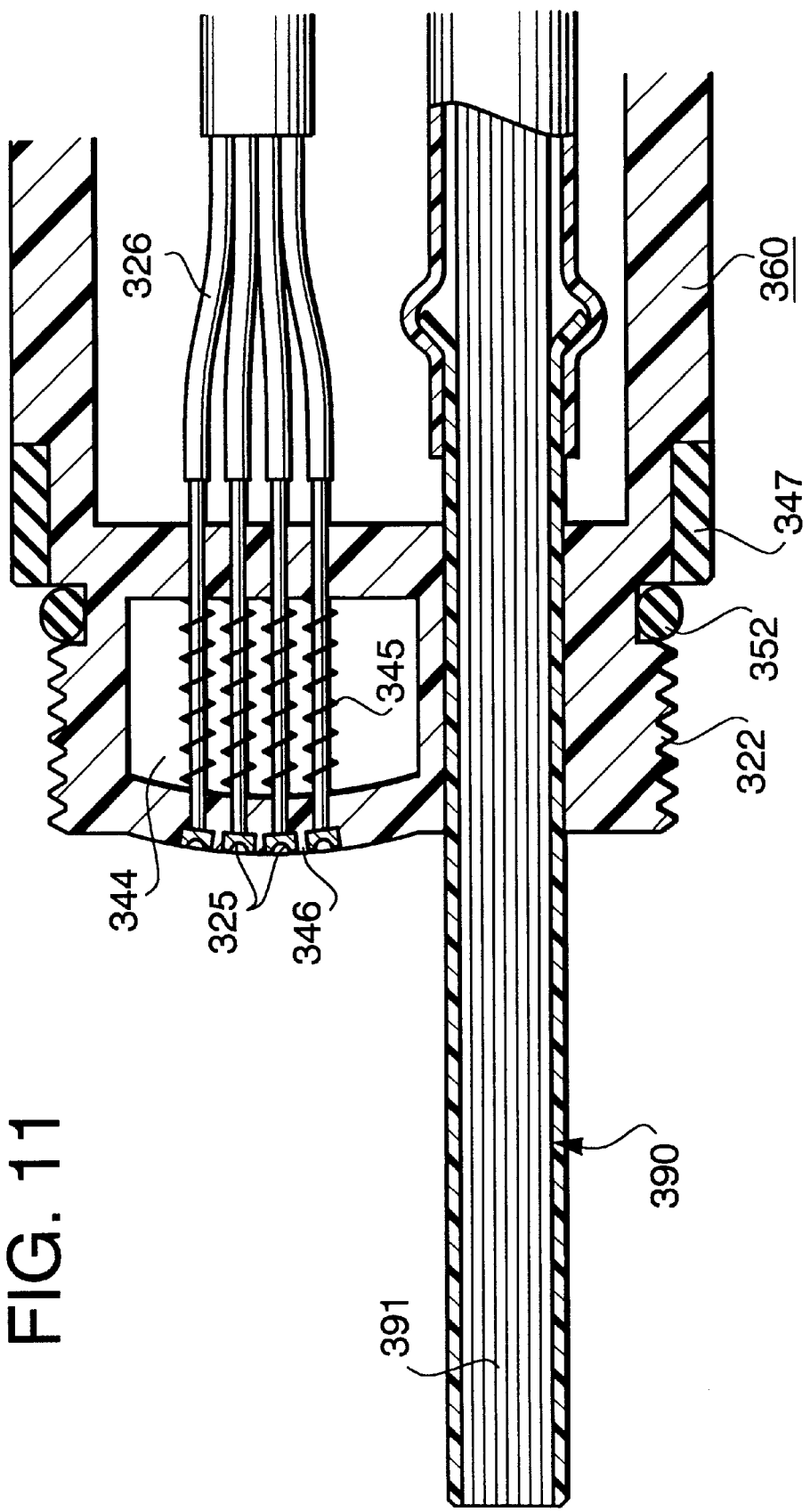
FIG. 11 is a sectional view of the mounting portion of FIG. 10.

The third embodiment of the present invention is described. FIG. 10 is a sectional view of a detachable unit and a mounting portion of the third embodiment. FIG. 11 is a sectional view of the mounting portion of FIG. 10. As shown in FIG. 10, a detachable unit 330 of the third embodiment includes a cylindrical unit body 370 and a cylindrical hood 320. The unit body 370 accommodates an object optical system 311 and a CCD 312. The object optical system 311 is covered by a view window 308 disposed at the front end of the unit body 370. The hood 320 is rotatable and slidable (in the direction of an axis of the unit body 370) on the unit body 370.

As shown in FIG. 11, a mounting portion 360 of the third embodiment is made of an insulation plastic. A fiber support pipe 390 (made of a stainless steel) is provided to the mounting portion 260, which accommodates a fiber bundle 391 therein. The fiber support pipe 390 is tightly fixed to the mounting portion 360 so that no water can enter into the mounting portion. The unit body 370 has a through-hole 341 through which the fiber support pipe 390 is inserted.

The hood 320 has an internal thread 321 and the mounting portion 360 has an external thread 322. The hood 320 is fixed to the mounting portion 360 by the engagement of the threads 321 and 322. In this state, the front end of the unit body 370 is urged (against the mounting portion 360) by a inner flange 328 of the hood 320. Thus, the unit body 370 is sandwiched between the hood 320 and the mounting portion 360 and held therebetween. When the detachable unit 330 is mounted to the mounting portion 360, the front end of the hood 320 and the front end of the unit body 370 are aligned on a same plane. The through-hole 341 is not positioned on the axis of the unit body 370, so that the relative rotational movement of the unit body 370 with respect to the mounting portion 360 is restricted by the fitting of the fiber support pipe 390 and the through-hole 341.

Pin-shaped first contacts 324 are provided to the rear surface of the unit body 370. The first contacts 324 are connected to a circuit board 313 provided in the unit body 370 via wires 323. Second contacts 325 (receptacles) are provided to a front wall 346 of the mounting portion 360 so that the first and second contacts 324 and 325 are faced with each other. The second contacts 325 are connected to wires 326 provided in the mounting portion 360.

A first O-ring 351 is provided to seal a gap between the outer surface of the unit body 370 and the inner surface of the hood 320. A second O-ring 352 is provided to seal a gap between the outer surface of the mounting portion 360 and the inner surface of the hood 320. Further, a third O-ring 342 is provided to seal the gap between the inner surface of the through-hole 341 and the fiber support pipe 390. This sealing arrangement prevents water from entering into a connecting portion of the first and second contacts 324 and 325. A rubber member 347 is lined along the outer surface of the mounting portion 360 so as to efficiently seal the clearance between the mounting portion 360 and the hood 320.

The mounting portion 360 is made of a plastic which is elastically deformable. The front wall 346 of the mounting portion 360 is curved to project frontward, by the force of the springs 345 provided in a recess 344 behind the front wall 46 as shown in FIG. 11. When the detachable unit 330 is mounted to the mounting portion 360, the front wall 346 abuts the rear end of the unit body 370 and is elastically deformed so that the front wall 346 becomes straight. Thus, the connection between the first and second contacts 324 and 325 is ensured.

Since the unit body 370 is made of plastic, the first contacts 324 and the view window 308 can be tightly fixed thereto. The rear end of the unit body 370 is sealed by a seal member 301. Since the mounting portion 360 is made of plastic, the second contacts 325 and the fiber support pipe 390 can be tightly fixed thereto. That is, the unit body 370 and the mounting portion 360 have waterproof structures.

As constructed above, the detachable unit 330 and the insertion tube can be sterilized separately, after removing the detachable unit 330 from the mounting portion. Thus, it is prevented that the CCD 312 breaks because of the heat caused by the autoclave. Further, the detachable unit 330 can be easily replaced without totally disassembling the insertion tube.

Figure 12:
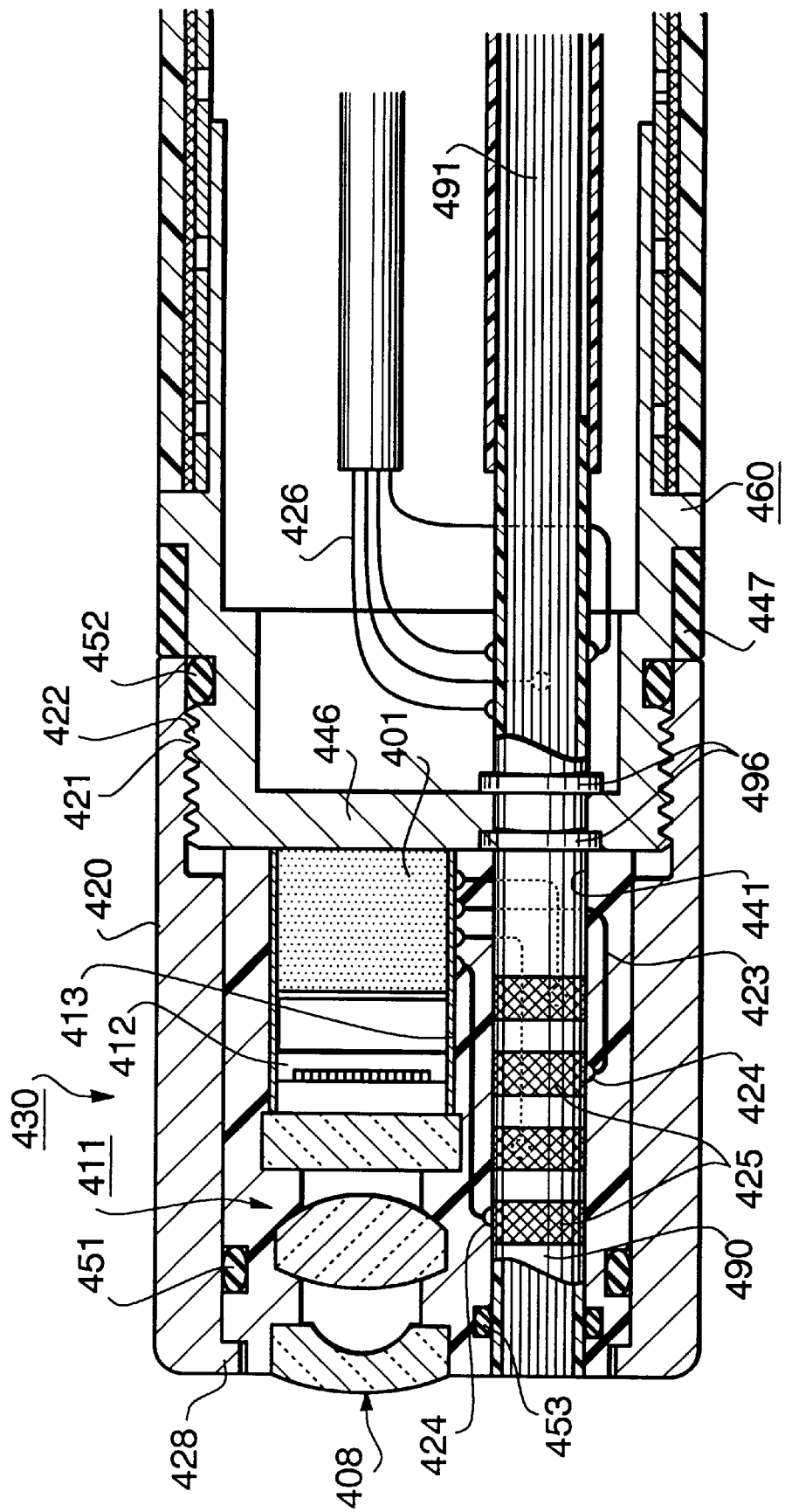
FIG. 12 is a sectional view of a detachable unit and a mounting portion of the fourth embodiment.

The fourth embodiment of the present invention is described. FIG. 12 is a sectional view of a detachable unit and a mounting portion of the fourth embodiment. As shown in FIG. 12, a detachable unit 430 of the fourth embodiment includes a cylindrical unit body 470 and a cylindrical hood 420. The unit body 470 accommodates an object optical system 411 and a CCD 412. The object optical system 411 is covered by a view window 408 disposed at the front end of the unit body 470. The hood 420 is rotatable and slidable (in the direction of an axis of the unit body 470) on the unit body 470.

As in the third embodiment, a fiber support pipe 490 (made of a stainless steel) is provided to a mounting portion 460, which a accommodates a fiber bundle 491 therein. The unit body 470 has a through-hole 441 into which the fiber support pipe 490 is inserted.

The hood 420 has an internal thread 421 and the mounting portion 460 has an external thread 422. The hood 420 is fixed to the mounting portion 460 by the engagement of the threads 421 and 422. In this state, the front end of the unit 470 is urged (against the mounting portion 460) by a inner flange 428 of the hood 420. Thus, the unit body 470 is sandwiched between the hood 420 and the mounting portion 460 and held therebetween. When the detachable unit 430 is mounted to the mounting portion 460, the front end of the hood 420 and the front end of the unit body 470 are aligned on a same plane. The through-hole 441 is not positioned on the axis of the unit body 470, so that the relative rotational movement of the unit body 470 with respect to the mounting portion 460 is restricted by the fitting of the pipe 490 and the through-hole 441.

First contacts 424 are provided to the inner surface of the through-hole 441. The first contacts 424 are connected to a circuit board 413 provided in the unit body 470 (via wires 423). Second contacts 425 are formed on the outer surface of the fiber support pipe 490 so that the first and second contacts 424 and 425 are in contact with each other. The second contacts 425 are connected to wires 426 provided in the mounting portion 460.

Figure 13:
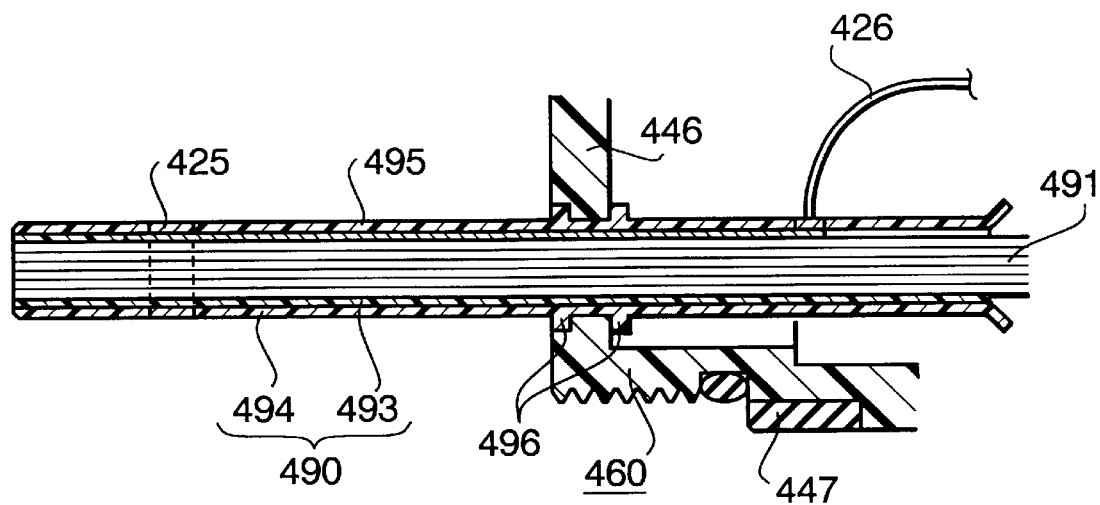
FIG. 13 is an enlarged view of a fiber support pipe of the fourth embodiment.

FIG. 13 is a sectional view of the fiber support pipe 490. The fiber support pipe 490 includes inner and outer pipes 493 and 494. The second contacts 425 are formed on the outer pipe 494. The outer pipe 494 is made of an insulating material except the second contacts 425. Conductive bands 495 (made of an electric conductive material) are formed on the inner pipe 493 so that the conductive bands 495 extends in the direction of the axis of the fiber support pipe 490, so as to electrically connect each second contact 425 and respective wire 426 provided in the mounting portion 460. The inner pipe 493 is made of an insulating material except the conductive bands 495.

The fiber support pipe 490 has a pair of flanges 496 sandwiching a front wall 446 of the mounting portion 460. With this, the fiber support pipe 490 is fixed to the mounting portion 460, preventing water from entering into the interior of the mounting portion 460. A first O-ring 451 is provided to seal a gap between the outer surface of the unit body 470 and the inner surface of the hood 420. A second O-ring 452 is provided to seal a gap between the outer surface of the mounting portion 460 and the inner surface of the hood 420. Further, a third O-ring 453 is provided seal the gap between the inner surface of the through-hole 441 and the outer surface of the fiber support pipe 490. A rubber member 447 is lined along the outer surface of the mounting portion 460 so as to efficiently seal the clearance between the mounting portion 460 and the hood 420.

The unit body 470 is made of a plastic, so that a view window 408 can be tightly fixed thereto. The rear end of the unit body 470 is sealed by a seal member 401. Thus, the unit body 470 has a waterproof structure. Further, due to the above described flanges 496, the mounting portion 460 also has a waterproof structure.

As constructed above, the detachable unit 430 and the insertion tube can be sterilized separately, after removing the detachable unit 430 from the mounting portion 460. Thus, it is prevented that the CCD 412 breaks because of the heat caused by the autoclave. Further, the detachable unit 430 can be easily replaced without totally disassembling the insertion tube.

Figure 14:
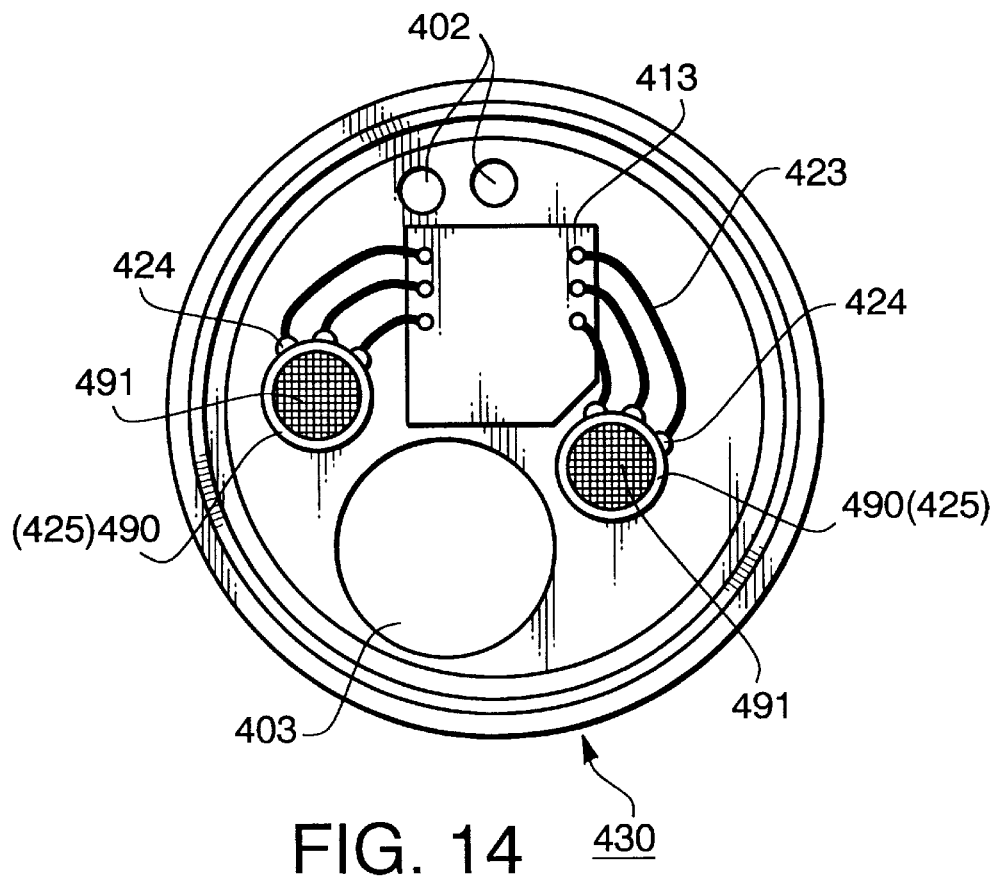
FIG. 14 is a schematic view showing a modification of the fourth embodiment.

FIG. 14 shows a modification of the fourth embodiment. In this modification, the mounting portion 460 has a plurality of fiber support pipes 490. Each fiber support pips 490 is provided with the above-described second contacts 425 thereon. In FIG. 14, channels for carrying air and water are denoted by 402, and a channel for medical instruments is denoted by 403.

Figure 15:
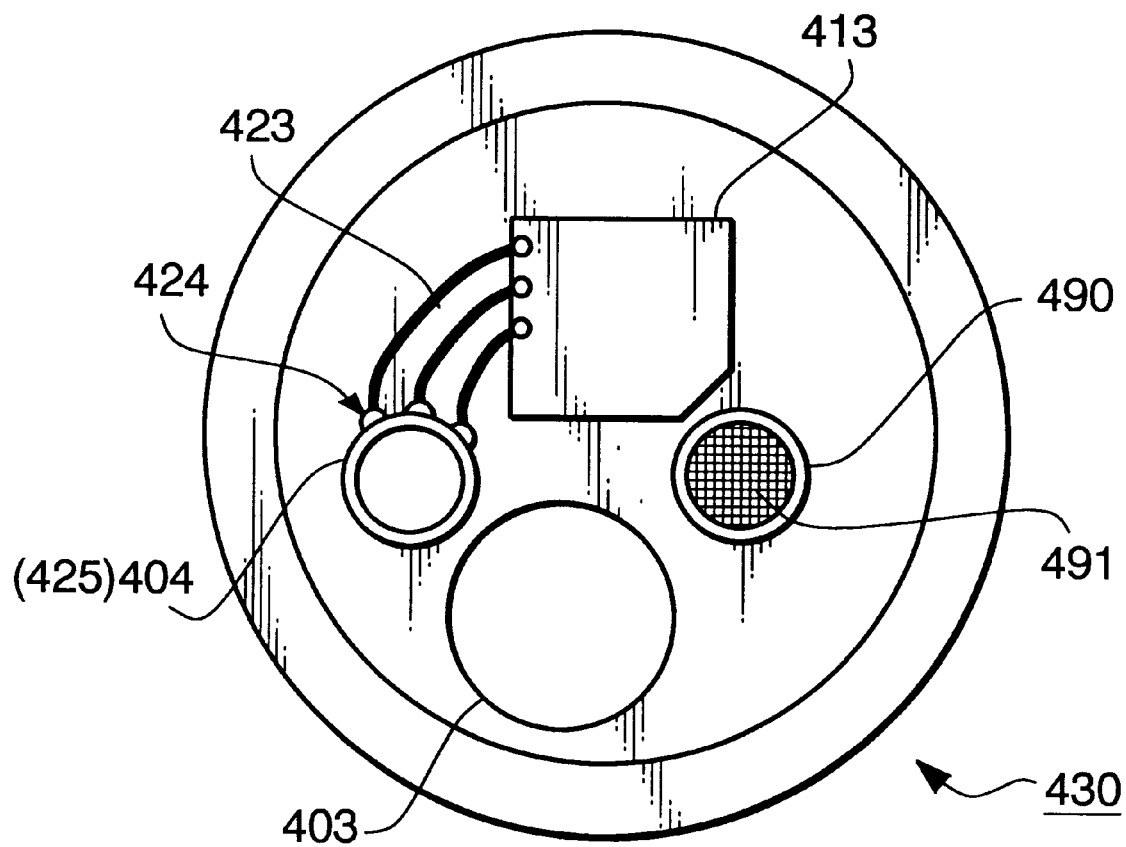
FIG. 15 is a schematic view showing another modification of the fourth embodiment.

FIG. 15 shows another modification of the fourth embodiment. In this modification, a fluid-carrying-pipe 404 is provided to the mounting portion 460, for carrying fluid into the human body cavity. The above-described second contacts 425 are provided on the fluid-carrying-pipe 404. The first contacts 424 are provided to the detachable unit 430 so that the first contacts 424 are in contact with the second contacts 425.

Figure 16:
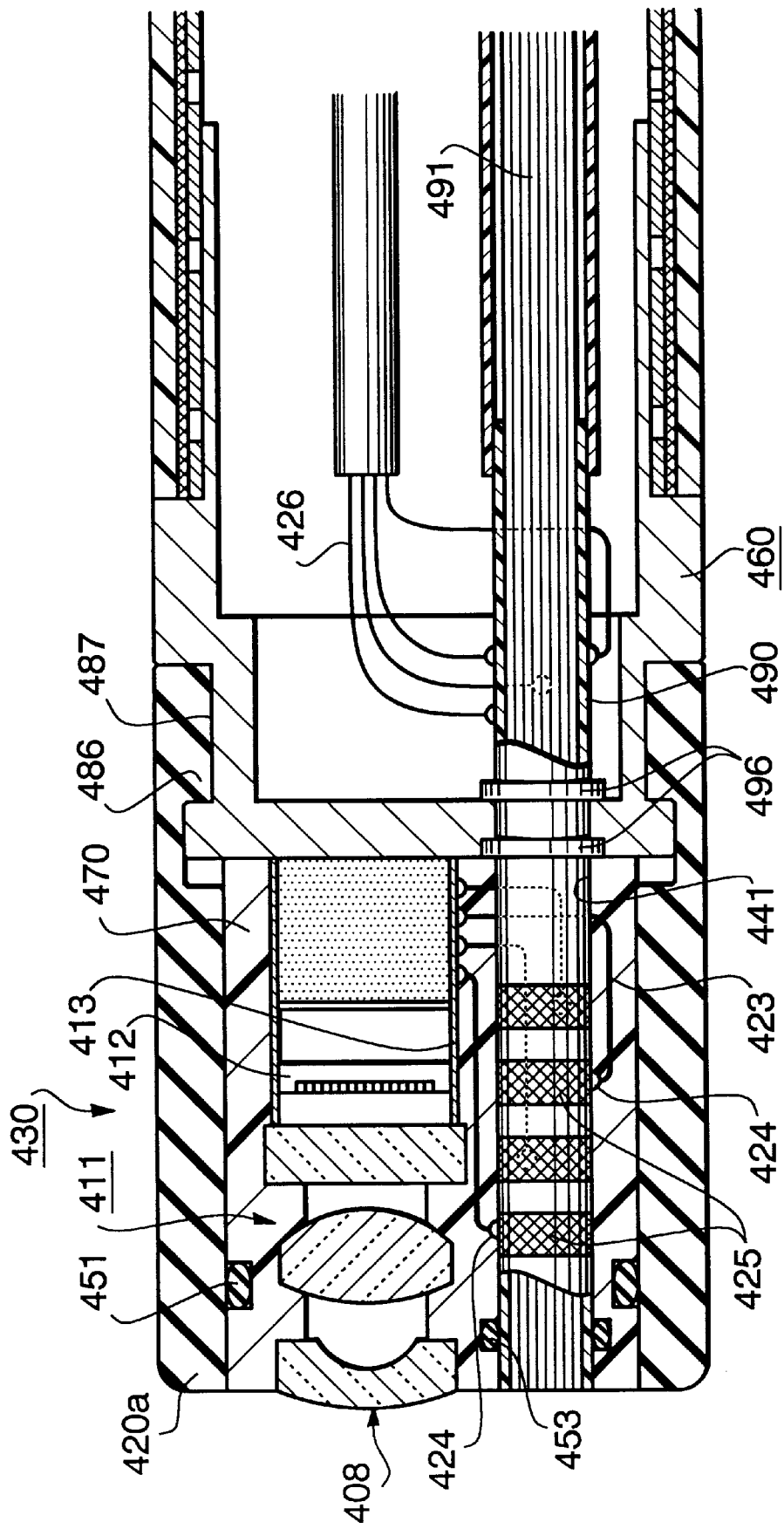
FIG. 16 is a sectional view showing further modification of the fourth embodiment.

FIG. 16 shows further modification of the fourth embodiment. In this modification, the hood 420a is made of plastic, such as polyurethane resin, silicon resin, vinyl chloride resin, or rubber. The hood 420 has hoods 486 (instead of internal thread 421) and the mounting portion 460 has holes 487 (instead of the external thread 422). By urging the hood 420a to the mounting portion 460, the hooks 486 is once deformed and engage the hole 487. With this, the mounting operation becomes easy.

Figure 17:
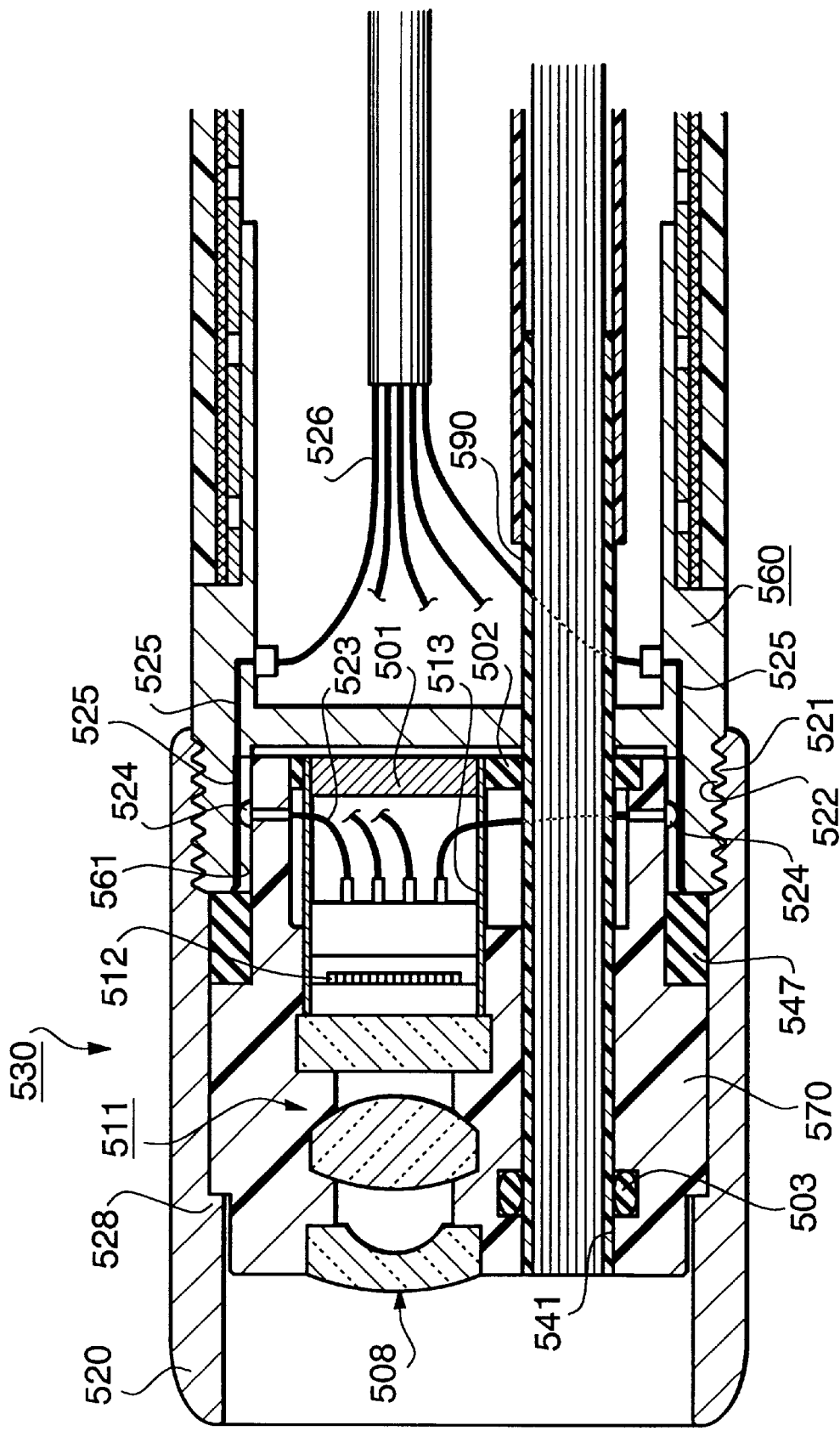
FIG. 17 is a sectional view of a detachable unit and a mounting portion of the fifth embodiment.

The fifth embodiment of the present invention is described. FIG. 17 is a sectional view of a detachable unit and a mounting portion of the fifth embodiment. As shown in FIG. 17, a detachable unit 530 of the fifth embodiment includes a cylindrical unit body 570 and a cylindrical hood 520. The unit body 570 accommodates an object optical system 511 and a CCD 512. The object optical system 511 is covered by a view window 508 disposed at the front end of the unit body 570. The hood 520 is rotatable and slidable (in the direction of an axis of the unit body 570) on the unit body 570.

The diameter of the rear part of the unit body 570 is smaller than the other part of the unit body 570. A mounting portion 560 has a cylindrical recess 561 which receives the rear part of the unit body 570. As in the fourth embodiment, a fiber support pipe 590 (made of a stainless steel) is provided to a mounting portion 560, which a accommodates a fiber bundle 591 therein. The unit body 570 has a through-hole 541 into which the fiber support pipe 590 is inserted.

The hood 520 has an internal thread 521. The mounting portion 560 has an external thread 522. By the engagement of the internal thread 521 and the external thread 522, the hood 520 is mounted to the mounting portion 560. In this state, the unit body 570 is urged (against the mounting portion 560) by a inner flange 528 of the hood 520. Thus, the unit body 570 is held between the hood 520 and the mounting portion 560 so that the rear part of the unit body 570 fit into the recess 561 of the mounting portion 560. The through-hole 541 is not positioned on the axis of the unit body 570, so that the relative rotational movement of the unit body 570 with respect to the mounting portion 560 is restricted by the fitting of the pipe 590 and the through-hole 541.

Figure 18:
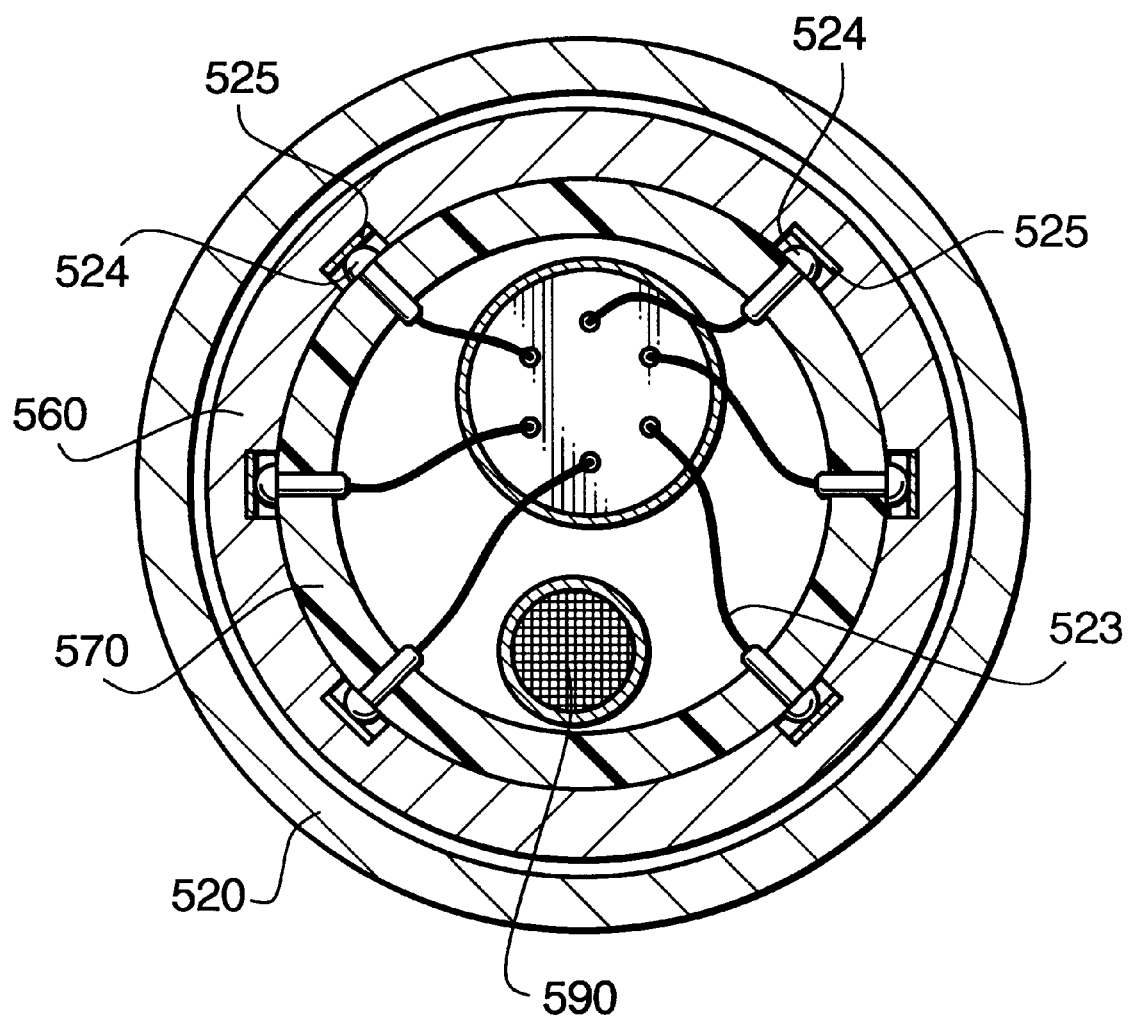
FIG. 18 is a schematic view showing an arrangement of contacts of the fifth embodiment.

First contacts 524 are formed on the outer surface of the rear part of the unit body 570. The first contacts 524 are connected to a circuit board 513 provided in the unit body 570 (via wires 523). Second contacts 525 are formed on the inner surface of the recess 561, which are electrically connected to the wires 526 provided in the mounting portion 560. The second contacts 525 extend in the direction of the axis of the unit body 570. As shown in FIG. 18, six couples of first and second contacts 524 and 525 are arranged on a circumference.

As shown in FIG. 17, a seal member 547 is provided to the outer surface of the rear part of the unit body 570 so that the front end of the mounting portion 560 abut the seal member 547. The seal member 547 prevents water from entering through the clearance between the internal thread 521 and the external thread 522.

The unit body 570 is made of plastic, so that a view window 508 can be tightly fixed thereto. The rear end of the unit body 570 is sealed by seal members 501 and 502. Thus, the unit body 570 has a waterproof structure. Further, since the fiber support pipe 590 is tightly fixed to the mounting portion 560, the mounting portion 560 also has a waterproof structure.

As constructed above, the detachable unit 530 and the insertion tube can be sterilized separately, after removing the detachable unit 530 from the mounting portion 560. Thus, it is prevented that the CCD 512 breaks because of the heat caused by the autoclave. Further, the detachable unit 530 can be easily replaced without totally disassembling the insertion tube.

Figure 19:
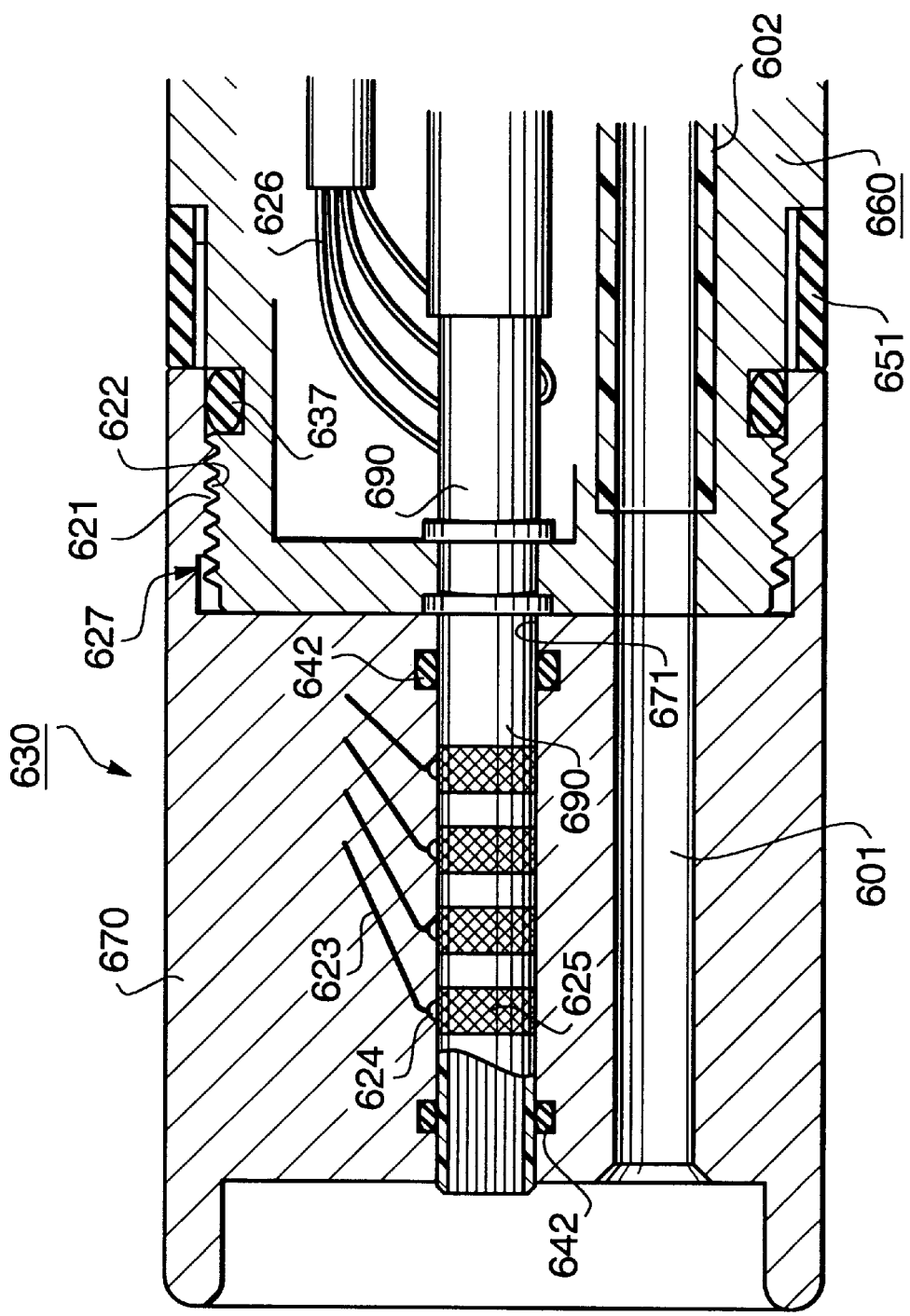
FIG. 19 is a sectional view of a detachable unit and a mounting portion of the sixth embodiment.

The sixth embodiment of the present invention is described. FIG. 19 is a sectional view of a detachable unit and a mounting portion of the sixth embodiment. An optical system and a CCD are omitted in FIG. 19. A detachable unit 630 of the sixth embodiment includes a unit body 670 and does not include a hood. A fiber support pipe 690 carrying a fiber bundle therein is provided to a mounting portion 660. A unit body 630 has a through hole 671 through which the fiber support pipe 690 is inserted. The fiber support pipe 690 is aligned with the axis of the mounting portion 660, while the through hole 671 is aligned with the axis of the unit body 670.

The unit body 670 has a recess 627 into which a front part of the mounting portion 660 fits. The unit body 670 has an internal thread 621 formed on the inner surface of the recess 627. The mounting portion 660 has an external thread 622 formed on the outer surface of the front part thereof. When the internal thread 621 and the external thread 622 engage with each other, the axis of the unit body 670 and the mounting portion 660 are aligned with each other, so that the fiber support pipe 690 is inserted in the through hole 671. By the engagement of the internal thread 621 and the external thread 622, the unit body 670 is mounted to the mounting portion 660. It is possible to rotate the unit body 670 for mounting the detachable unit 630 to the mounting portion 660, since the fiber support pipe 690 is positioned at the center axis of the detachable unit 630.

First contacts 624 and second contacts 625 are provided for electrical connection. Since the first and second contacts 624 and 625 are constructed in a similar manner to the first and second contacts 424 and 425 of the fourth embodiment (FIG. 12), the detailed description thereof is omitted.

In order to introduce a medical instrument into a human body cavity, a first channel 601 is provided to the unit body 670. A second channel 602 is provided through the insertion tube, so that the front end thereof is fixed to the mounting portion 660. When the detachable unit 630 is mounted to the mounting portion 660, the first and second channels 601 and 602 are aligned with each other. Thus, a medical instrument such as forceps can be introduced through the channels 601 and 602. It is necessary to accurately adjust the rotational position of the unit body 670 with respect to the mounting portion 660 so as to align the first and second channels 601 and 602. For this purpose, an adjuster nut 651 engages an external thread formed on the outer surface of the mounting portion 660. The rear end of the unit body 670 abuts the adjuster nut 651. With this, the rotational position of the unit body 670 with respect to the mounting portion 660 can be adjusted accurately, by rotating the adjuster nut 651.

A pair of O-rings 642 are provided to the outer surface of the front and rear ends of the fiber support pipe 690, which seals the gap between the fiber support pipe 690 and the unit body 670. This arrangement prevents water from entering into the connecting portion of the first and second contacts 624 and 625. An O-ring 637 is provided to the outer surface of the front part of the mounting portion 660, which prevents the loosening of the engagement of the threads 621 and 622.

As in the previous embodiments, the unit body 670 and the mounting portion 660 have waterproof structures. As constructed above, the detachable unit 630 and the insertion tube can be sterilized separately, after removing the detachable unit 630 from the mounting portion 660. Thus, it is prevented that the CCD breaks because of the heat caused by the autoclave. Further, the detachable unit 630 can be easily replaced without totally disassembling the insertion tube. In the sixth embodiment, it is possible to use a Bayonet mechanism instead of the threads 621 and 622.

Figure 20:
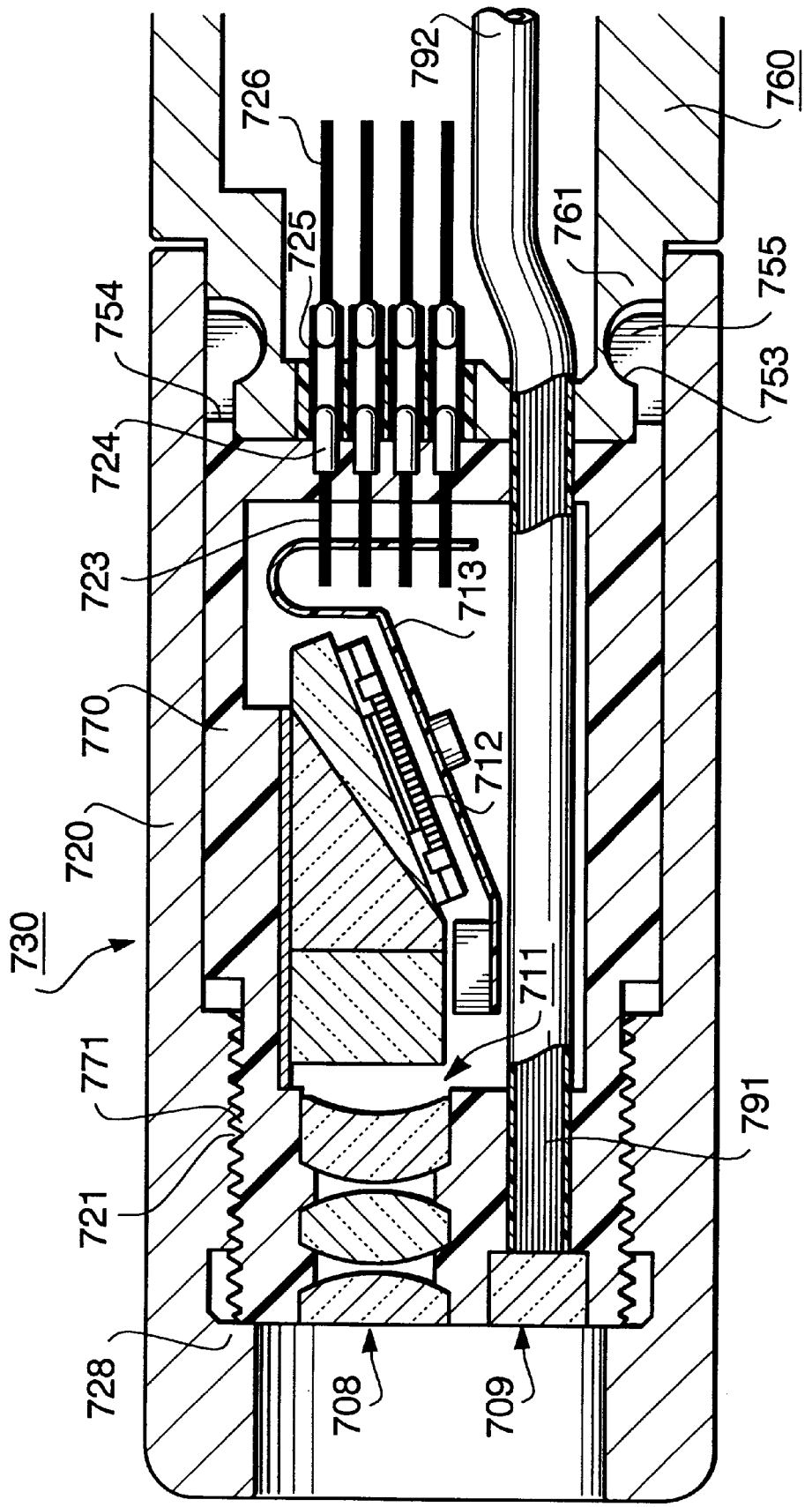
FIG. 20 is a sectional view of a detachable unit and a mounting portion of the seventh embodiment.

The seventh embodiment of the present invention is described. FIG. 20 is a sectional view of a detachable unit and a mounting potion of the seventh embodiment. As shown in FIG. 20, a detachable unit 730 of the seventh embodiment includes a cylindrical unit body 770 and a cylindrical hood 720. The unit body 770 accommodates an object optical system 711 and a CCD 712. The object optical system 711 is covered by a view window 708 disposed at the front end of the unit body 770.

A mounting portion 760 of the seventh embodiment includes a front part 761 having a peripheral groove 753 formed on the outer surface thereof. The unit body 770 has a skirt 754 protruded rearward from the circumference of the hood 720. The skirt 754 has inwardly projecting portion 755 formed at the rear end thereof, which engages the peripheral groove 753 of the mounting portion 760. The skirt 754 has several slits (not shown) so that the skirt 754 is elastically deformable. The skirt 754 and the peripheral groove 753 constitute a click mechanism. Due to the click mechanism, the unit body 770 is mounted to the mounting portion 760. Optionally, it is possible to replace the inwardly projecting portion 755 by several projections. In such case, the peripheral groove 753 can be replaced by holes which receives the projections.

An external thread 771 is formed at the outer surface of the front part of the unit body 770. An internal thread 721 is formed on the inner surface of the hood 720. The hood 720 is fixed to the unit body 770 by the engagement of the internal thread 721 and the external thread 771. When the unit body 770 is fixed to the mounting portion 760 and when the hood 720 is fixed to the unit body 770, the skirt 754 is held by the hood 720 (from outward) so that the inwardly projecting portion 755 does not drop out of the peripheral groove 753.

First contacts 724 are proved at the rear end of the unit body 770. The first contacts 724 are connected to a circuit board 713 provided in the unit body 770 (vias wires 723). The first contacts 724 are pin-shaped and protruded in the direction parallel to the axial direction of unit body 770. Second contacts 725 are provided to the front end of mounting portion 760. The second contacts 725 are tubular-shaped so that the second contacts 725 respectively receives the first contacts 724.

Before mounting the detachable unit 730 to the mounting portion 760, the hood 720 is moved frontward so that the hood 720 does not prevent the skirt 754 from deforming. Then, the unit body 770 is moved toward to the mounting portion 760 so that the inwardly projecting portion 755 of the skirt 754 engages the cylindrical groove 753. With this, the unit body 770 is fixed to the mounting portion 760. Next, the hood 720 is fixed to the unit body 770 by the engagement of the threads 721 and 771. In this state, the front end of the unit body 770 is urged (against the mounting portion 760) by a inner flange 728 of the hood 720. Thus, the unit body 770 is sandwiched between the hood 720 and the mounting portion 760 and held therebetween.

The unit body 770 and the mounting portion 760 have waterproof structures as in the previous embodiments. As constructed above, the detachable unit 730 and the insertion tube can be sterilized separately, after removing the detachable unit 730 from the mounting portion 760. Thus, it is prevented that the CCD 712 breaks because of the heat caused by the autoclave. Further, the detachable unit 730 can be easily replaced without totally disassembling the insertion tube.

Figure 21:
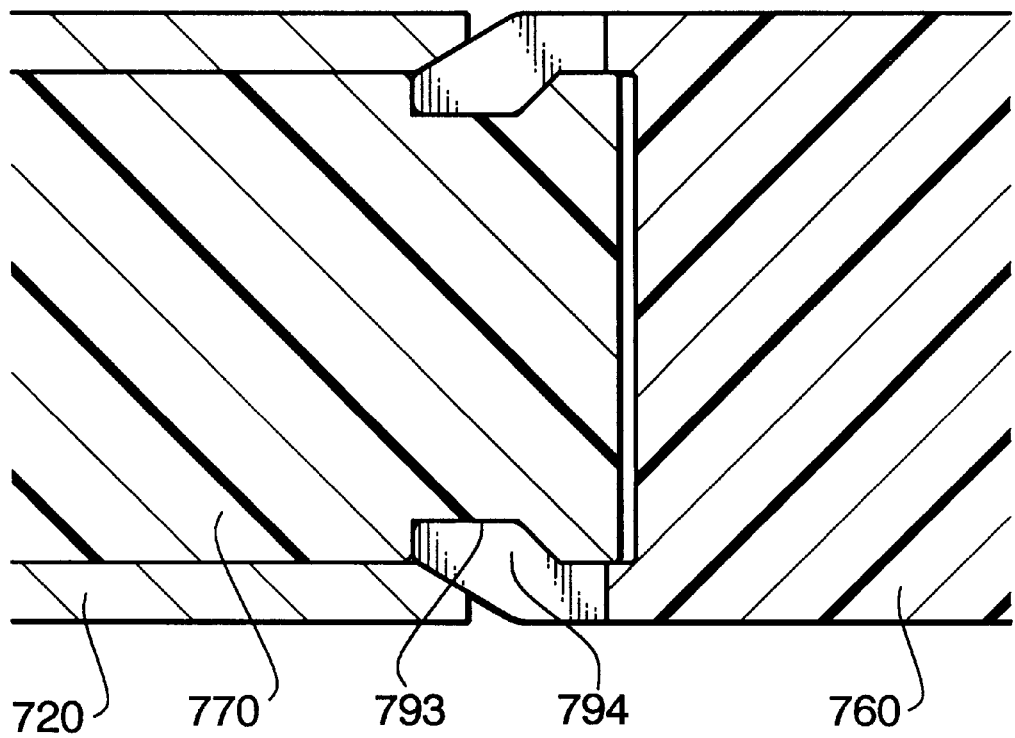
FIG. 21 is a schematic view showing a modification of the seventh embodiment.

FIG. 21 shows a modification of the seventh embodiment. In this modification, a peripheral groove 793 is formed on outer surface of the unit body 770. Further, a hooks 794 are provided to the mounting portion 760. The hooks 794 and the peripheral groove 793 constitute a click mechanism. That is, the unit body 770 is mounted to the mounting portion 760 by the engagement of the hooks 794 and the peripheral groove 793. When the hood 720 (not shown in FIG. 21) is fixed to the unit body 770, the hooks 794 is held (from outward) by the hood 720 so that the hooks 794 do not drop out from the peripheral groove 793.

Figure 22:
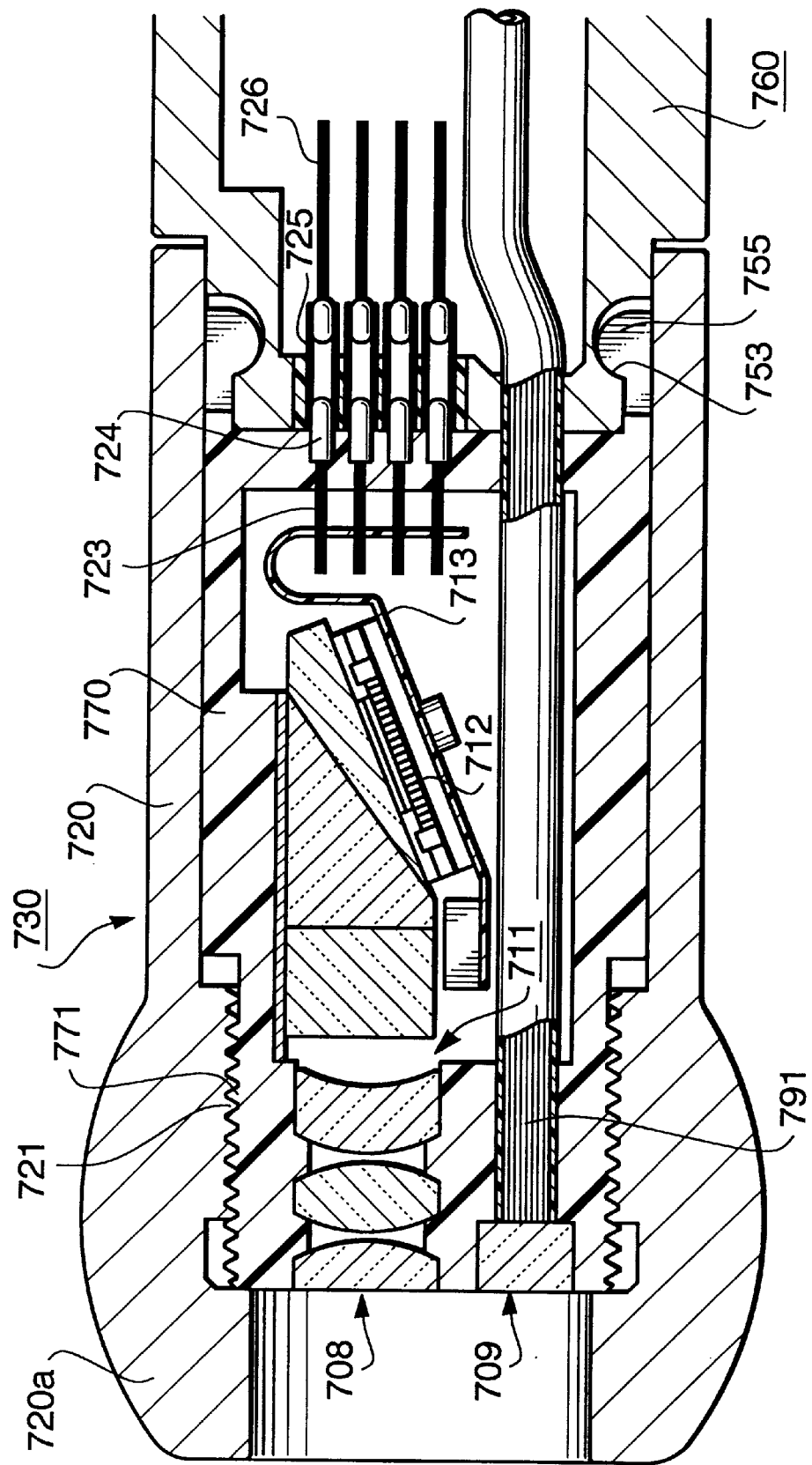
FIG. 22 is a schematic view showing another modification of the seventh embodiment.

FIG. 22 shows another modification of the seventh embodiment. In this modification, the front end portion of the hood 720a is round-shaped and is protruded from the front end of the unit body 770. With this, it is easy to insert the insertion tube into the cavity of the human body cavity.

Figure 23:
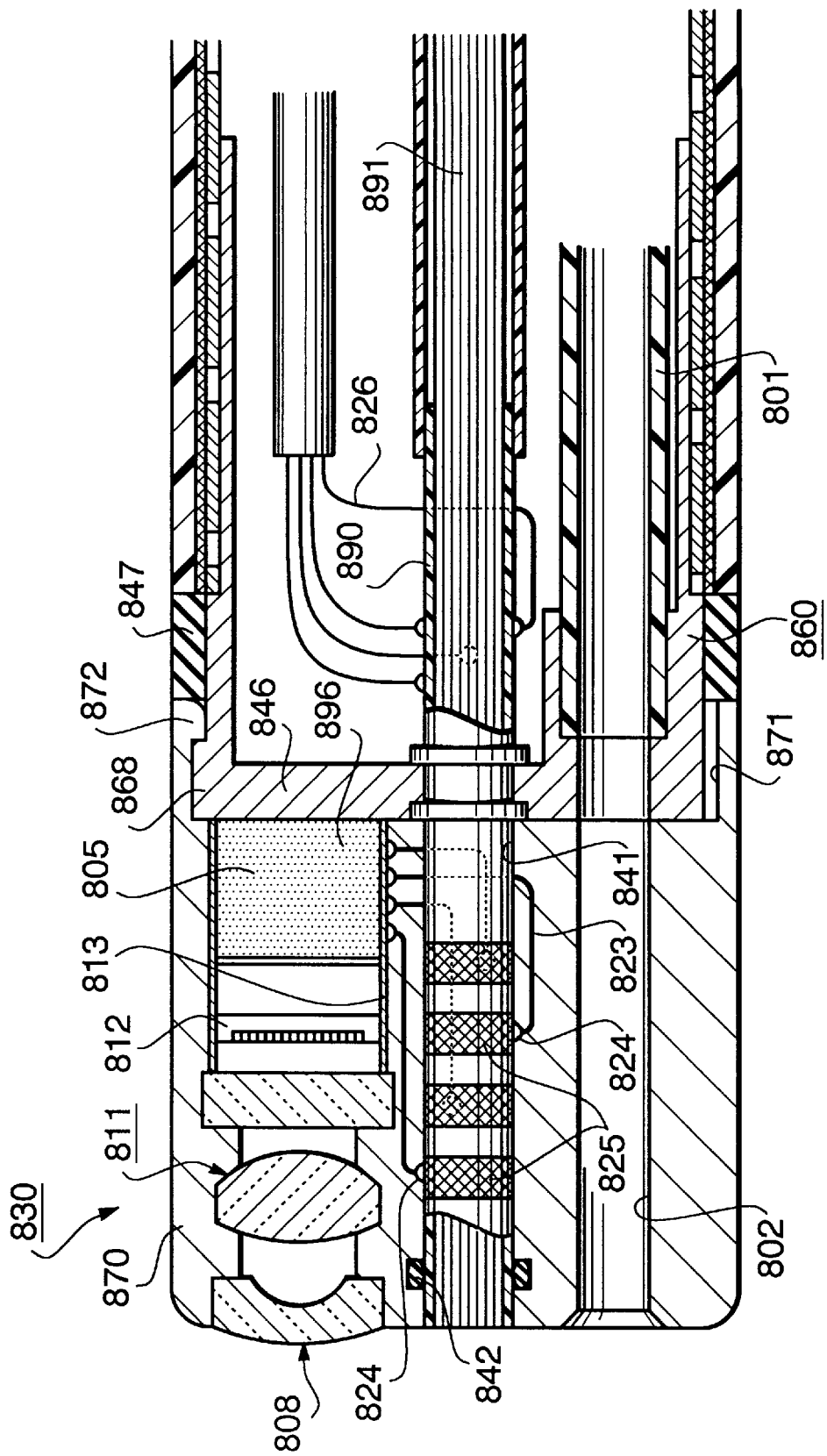
FIG. 23 is a sectional view of a detachable unit and a mounting portion of the eighth embodiment.

The eighth embodiment of the present invention is described. FIG. 23 is a sectional view of a detachable unit and a mounting portion of the eighth embodiment. As shown in FIG. 23, a detachable unit 830 to the eighth embodiment includes a cylindrical unit body 870. The unit body 870 accommodates an object optical system 811 and a CCD 812. The object optical system 811 is covered by a view window 808 disposed at the front end of the unit body 870.

Like the fourth embodiment (shown in FIG. 12), a fiber supporting pipe 890 is provided to a mounting portion 860, which accommodates a fiber bundle 891 therein. The fiber support pipe 890 has a pair of flanges 896 sandwiching a front wall 846 of the mounting portion 860, so that the fiber support pipe 890 is tightly fixed to the mounting portion 860. The unit body 870 has a through-hole 841 through which the fiber supporting pipe 890 is inserted. Further, the unit body 870 has a recess 871 at the rear end thereof into which the front end of the mounting portion 860 fits. As in the sixth embodiment, the fiber support pipe 890 is positioned at the center axis of the unit body 870, so that the unit body 870 can be rotated with respect to the mounting portion 860.

Figure 24:
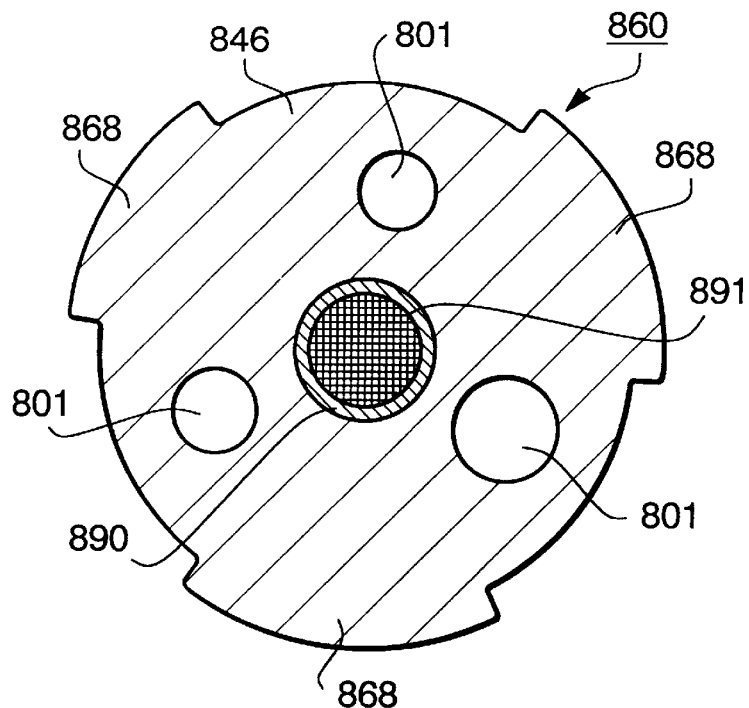
FIG. 24 is a sectional view of a click mechanism of the detachable unit of FIG. 23.
Figure 25:
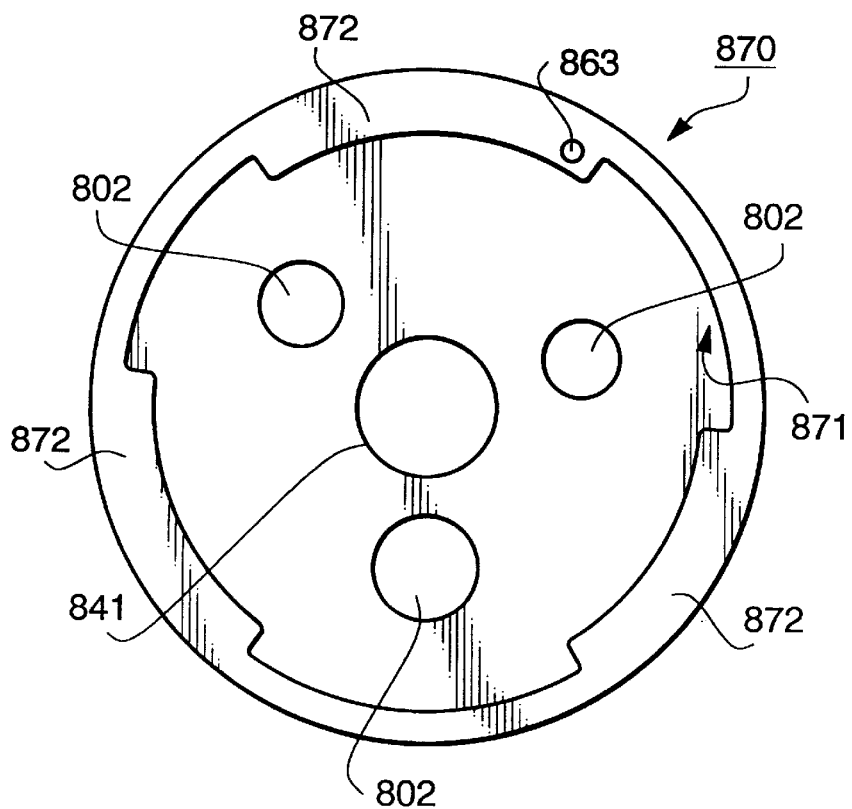
FIG. 25 is a rear view of a click mechanism of the mounting portion of FIG. 23.
Figure 26:
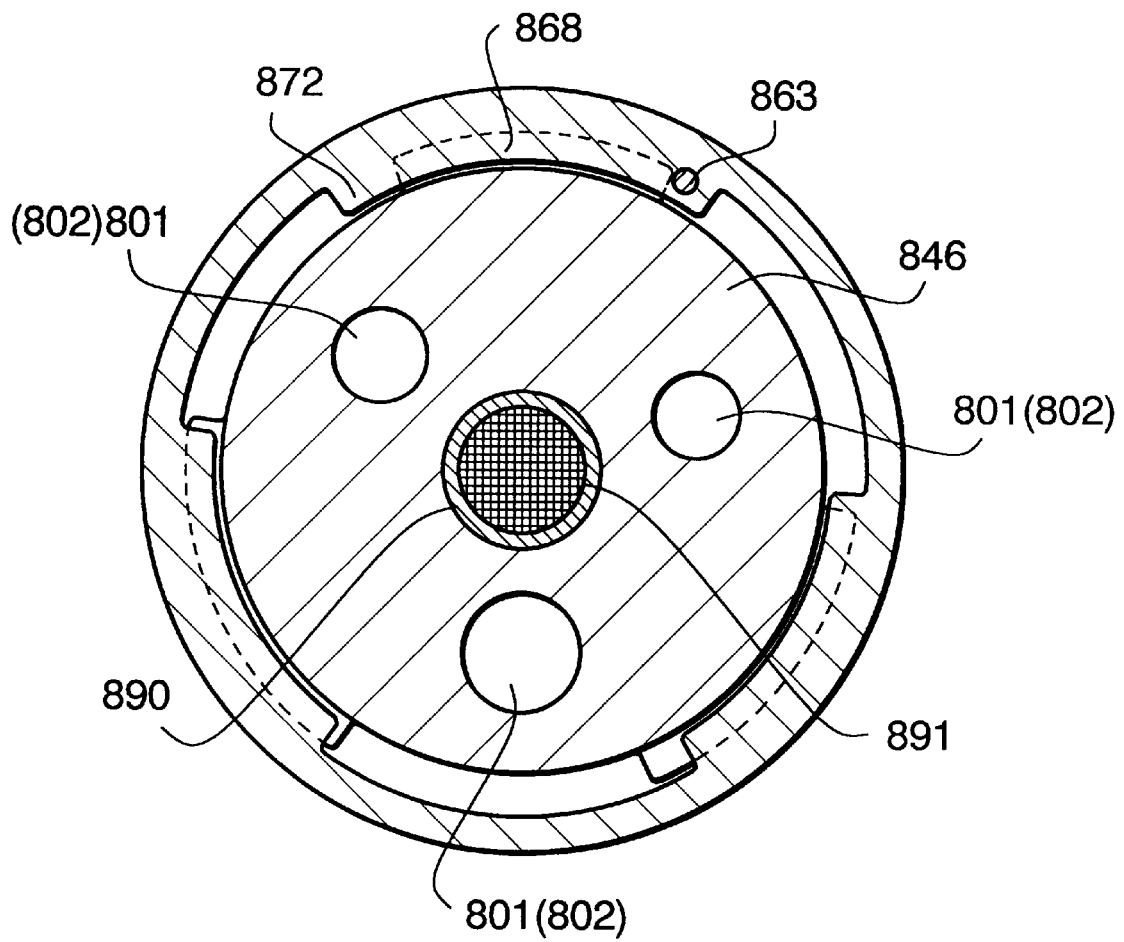
FIG. 26 is a sectional view of a click mechanism.

FIGS. 23, 24 and 25 illustrate a bayonet mechanism for mounting the detachable unit 830 to the mounting portion 860. As shown in FIG. 24, has three first claws 868 are protruding outward from the circumference of the front part of the mounting portion 860. As shown in FIG. 25, three second claws 872 are protruded from the inward inner surface of the recess 871. A space is formed between the second claw 872 and the bottom surface of the recess 871 (as shown in FIG. 23), which receives the first claw 868 therein. By fitting the front part of the mounting portion 860 to the recess 871 and by rotating the unit body 870, the first claws 868 and the second claws 872 engage with each other as shown in FIG. 26. In this state, the unit body 870 is securely fixed to the mounting portion 860. When the detachable unit 830 is mounted to the mounting portion 860, the front end of the hood 820 and the front end of the unit body 870 are aligned on a same plane.

As shown in FIG. 24, channels 801 for carrying water and air are provided to the unit body 870. Similarly, as shown in FIG. 25, channels 802 for carrying water and air are provided to the mounting portion 860. It is necessary to accurately adjust the rotational position of the unit body 870 with respect to the mounting portion 860 so as to align the channels 801 and 802. For this purpose, a stopper 863 is provided to the recess 871 so that the rotation of the unit body 870 is stopped with the first claw 868 abuts the stopper 863. With such an arrangement, the detachable unit 830 can be easily mounted to and removed from the mounting portion 860.

First contacts 824 are provided to the inner surface of the through-hole 841. The first contacts 824 are connected to a circuit board 813 provided in the unit body 870 (via wires 823). Second contacts 825 are formed on the outer surface of the fiber support pipe 890 so that the first and second contacts 824 and 825 are in contact with each other. The second contacts 825 are connected to wires 826 provided in the mounting portion 860. The first and second contacts 824 and 825 are connected in a similar manner with the fourth embodiment (FIG. 16).

A rubber member 847 is lined along the outer surface of the mounting portion 860 so as to seal the clearance between the mounting portion 860 and the unit body 870. The sealing member 847 prevents the loosening of the first and second claws 868 and 872, since the rubber member 847 urges the second claws 868 against the first claws 871. An O-ring 842 is provided to seal a gap between the inner surface of the through-hole 841 and the outer surface of the fiber support pipe 890. With this, the first contacts 824 and second contacts 825 are free from the water.

A view window 808 is tightly fixed to the unit body 870 and the rear end of the unit body 870 is sealed by a seal member 805. Thus, the unit body 870 has a waterproof structure. Further, since the fiber support 890 is tightly fixed to the mounting portion 860 (due to the flanges 896), the mounting portion 860 also has a waterproof structure.

As constructed above, the detachable unit 830 and the insertion tube can be sterilized separately, after removing the detachable unit 830 from the mounting portion 860. Thus, it is prevented that the CCD 812 breaks because of the heat caused by the autoclave. Further, the detachable unit 830 can be easily replaced without totally disassembling the insertion tube.

Figure 27:
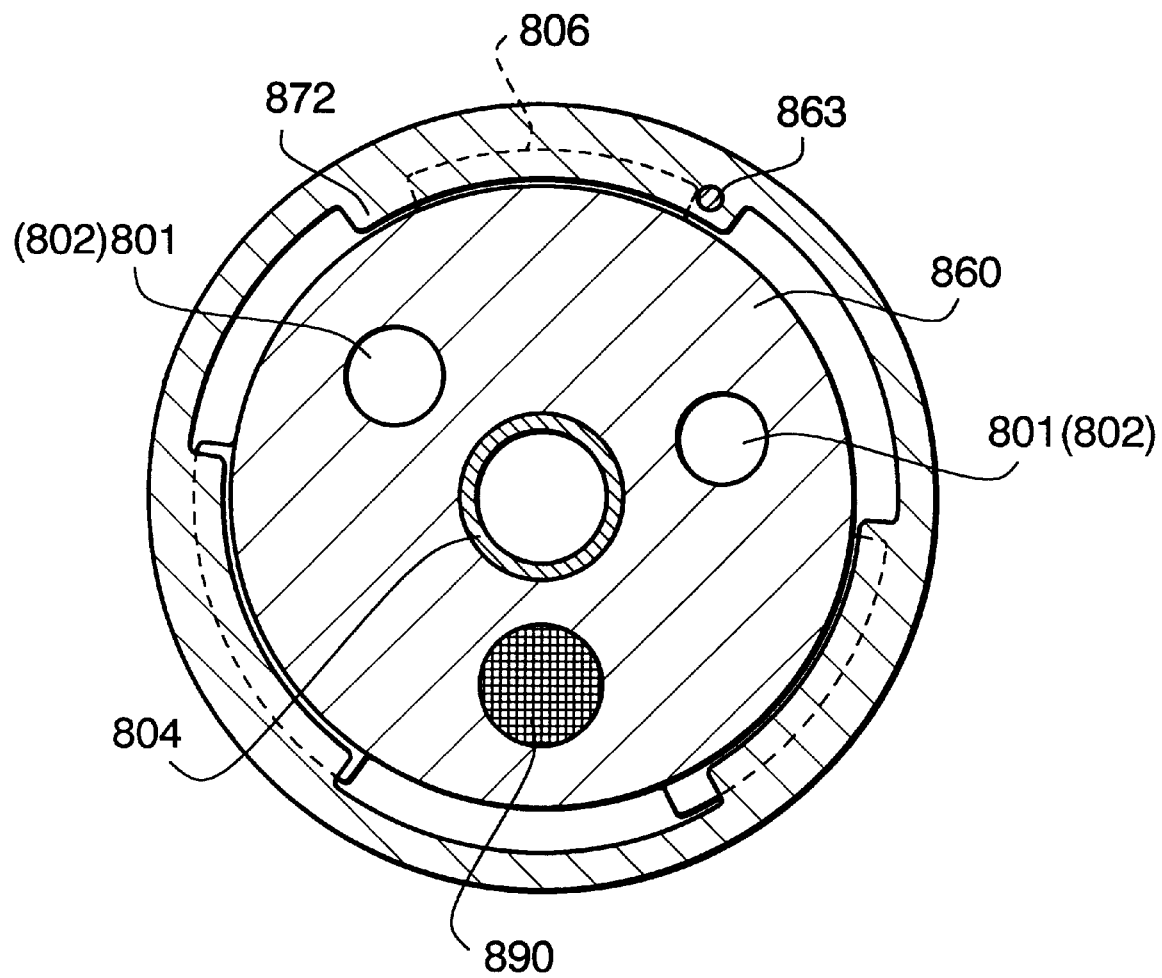
FIG. 27 is a schematic view showing a modification of the eighth embodiment.

FIG. 27 shows a modification of the eighth embodiment. In this embodiment, a fluid-carrying-pipe 804 is provided to the center of the mounting portion 860 (not shown in FIG. 27). The fiber 891 is supported by a channel 890a instead of the fiber support pipe 890. The above-described second contacts 825 (not shown in FIG. 27) are provided on the fluid-carrying-pipe 804.

Figure 28:
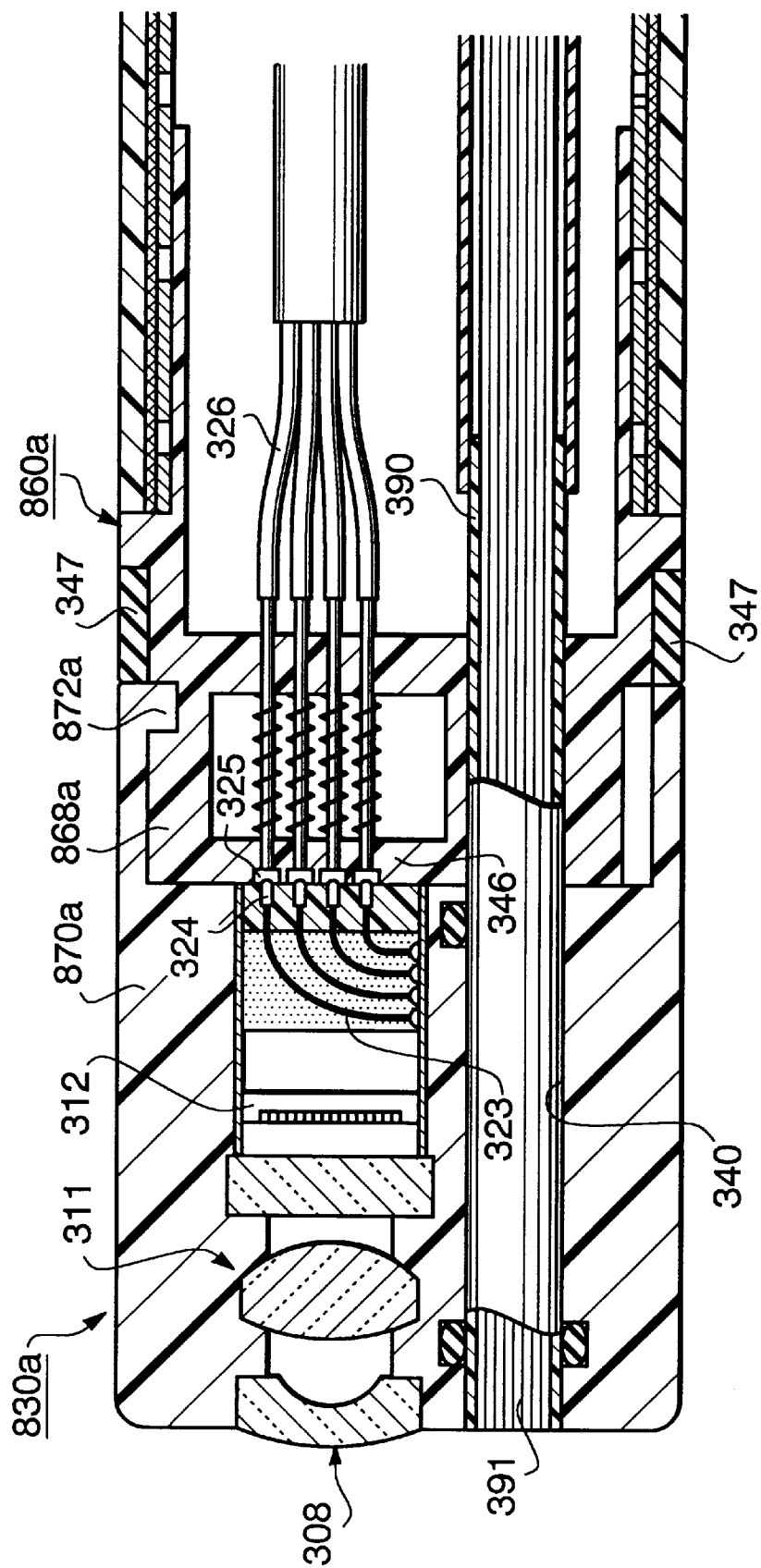
FIG. 28 is a sectional view showing another modification of the eighth embodiment.

FIG. 28 shows another modification of the eighth embodiment. In a detachable unit 830a of this modification, electric components are constructed in a similar manner to the third embodiment (FIG. 10). A mounting portion 860a is constructed in a similar manner to the third embodiment (FIG. 10), except the mounting portion 860a has first claws 868a. In FIG. 28, components having the same structures as the second embodiment are denoted by same reference numbers. The detachable unit 830a includes a unit body 870a, having second claws 872a which engage with the first claws 868a of the mounting portion 860a. The first and second claws 868a and 872a constitute a bayonet mechanism.

Figure 29:
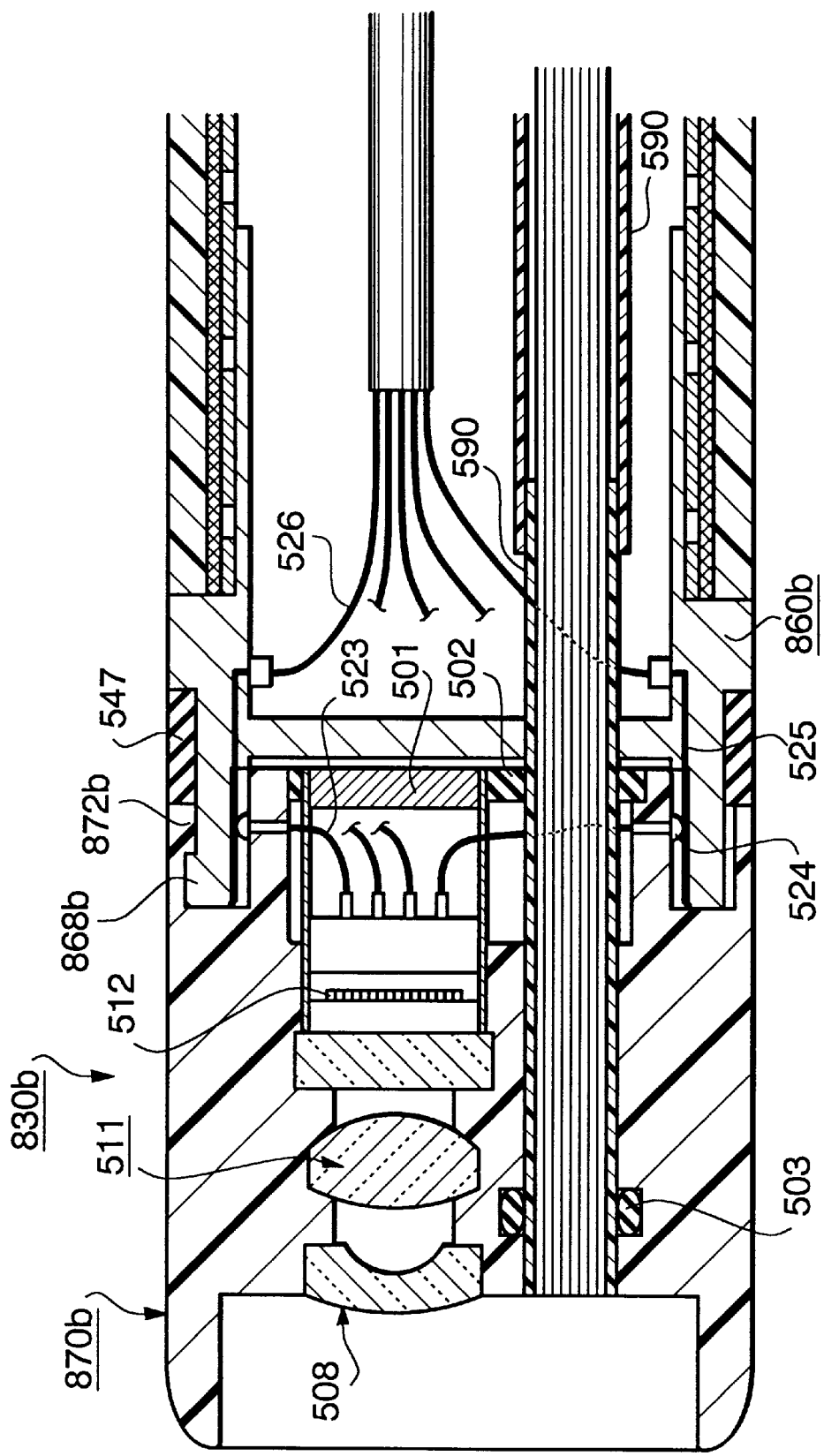
FIG. 29 is a sectional view showing further modification of the eighth embodiment.

FIG. 29 shows further modification of the eighth embodiment. In a detachable unit 830b of this modification, electric components are arranged in a similar manner to the fifth embodiment (FIG. 17). A mounting portion 860b is constructed in a similar manner to the third embodiment (FIG. 17), except the mounting portion 860b has first claws 868b. In FIG. 29, components having the same structures as the second embodiment are denoted by same reference numbers. The detachable unit 830b includes a unit body 870b, having second claws 872b which engage the first claws 868b of the mounting portion 860b. The first and second claws 868b and 872b constitute a bayonet mechanism.

Figure 30:
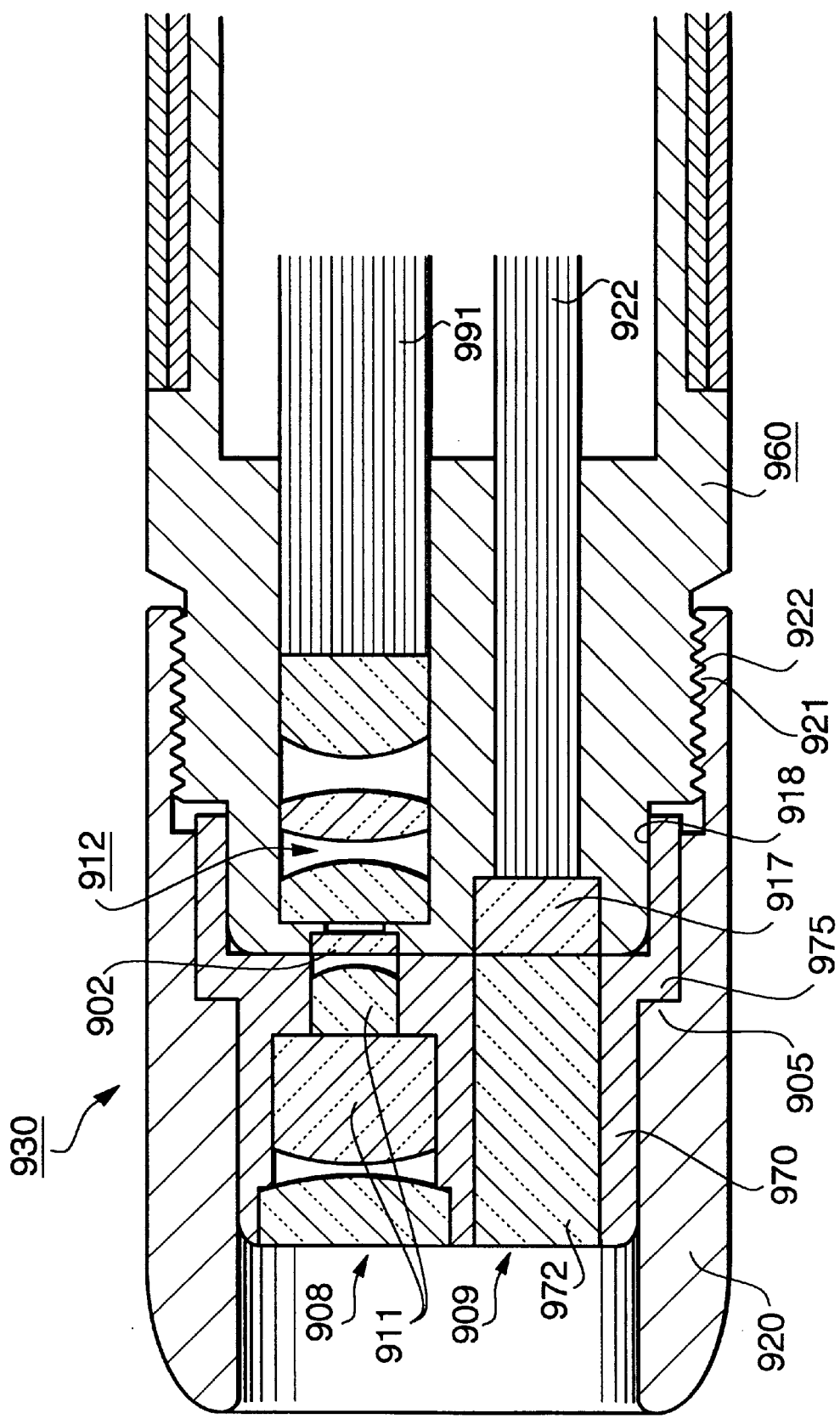
FIG. 30 is a sectional view of a detachable unit and a mounting portion of the ninth embodiment.

The ninth embodiment of the present invention is described. FIG. 30 is a sectional view of an adapter and a mounting portion of the ninth embodiment. Different from the previous embodiments, an adapter 930 having no CCD is provided in the ninth embodiment. The adapter 930 includes a cylindrical adapter body 970 and a hood 920. The adapter body 930 accommodates a first optical system 911. The first optical system 911 is covered by a view window 908 provided to the adapter body 970. A mounting portion 960 of the ninth embodiment accommodates a second optical system 912 having an optical axis being aligned with an optical axis of the first optical system 911. The first and second optical systems 911 and 912 constitute an object optical system. An image-fiber-bundle 991 is provided to the mounting portion 960, for carrying image formed by the object optical system to a not-shown manipulator. The tip of the image-fiber-bundle 991 is fixed to the mounting portion 960 (behind the second optical system 912). The second optical system 912 is covered by a cover glass 902 provided to the mounting portion 960.

In order to illuminate an object, an illumination-fiber-bundle 992 is provided to the mounting portion 960 for carrying illumination light. The fiber bundles 991 and 992 extend through the insertion tube in parallel to each other. A cover glass 917 is provided at the front side of the illumination-fiber-bundle 992. An illumination window 909 is provided to the unit body 970, which includes a glass rod 972.

The adapter body 970 has a recess 918 into which a front part of the mounting portion 960 fits. The hood 920 has an internal thread 921 which engages an external thread 922 formed on the mounting portion 960. The hood 920 has a shoulder portion 905 which abuts a step portion 975 formed on the outer surface of the unit body 970. The hood 920 is rotatable and slidable (in the direction of an axis of the adapter body 970) on the adapter body 970, so that the hood 920 is fixed to the mounting portion 960 by engaging the internal thread 921 with the external thread 922. In this state, the adapter body 970 is urged by the shoulder portion 905 against the mounting portion 960. With this, the adapter 930 is surely fixed in the mounting portion 960. The rotational position of the adapter body 970 with respect to the mounting portion 960 is determined by not-shown rotation stoppers provided to the adapter body 970 and the mounting portion 960. In this state, the optical axes of the first optical system 911 and the second optical system 912 are aligned with each other. Further, the glass rod 972 and the cover glass 917 are faced with each other. On removing the adapter 930 from the mounting portion 960, the hood 920 is rotated to loosen the engagement of threads 921 and 922. Then, the adapter body 970 can be removed from the mounting portion 960.

As constructed above, it is possible to replace the optical system (provided in the adapter 930) only by removing the hood 920 from the mounting portion 960. Thus, the replacement of the optical system becomes easy. Further, since the front end of the hood 930 is protruded from the front end of the unit body 970, it is possible to urge a sticky surface of a human body cavity away from the detachable unit 30, thereby to keep an appropriate distance between the surface and the object optical system. In this embodiment, it is possible to change the field view, by replacing the adapter 930 with another adapter having different optical system.

Figure 31:
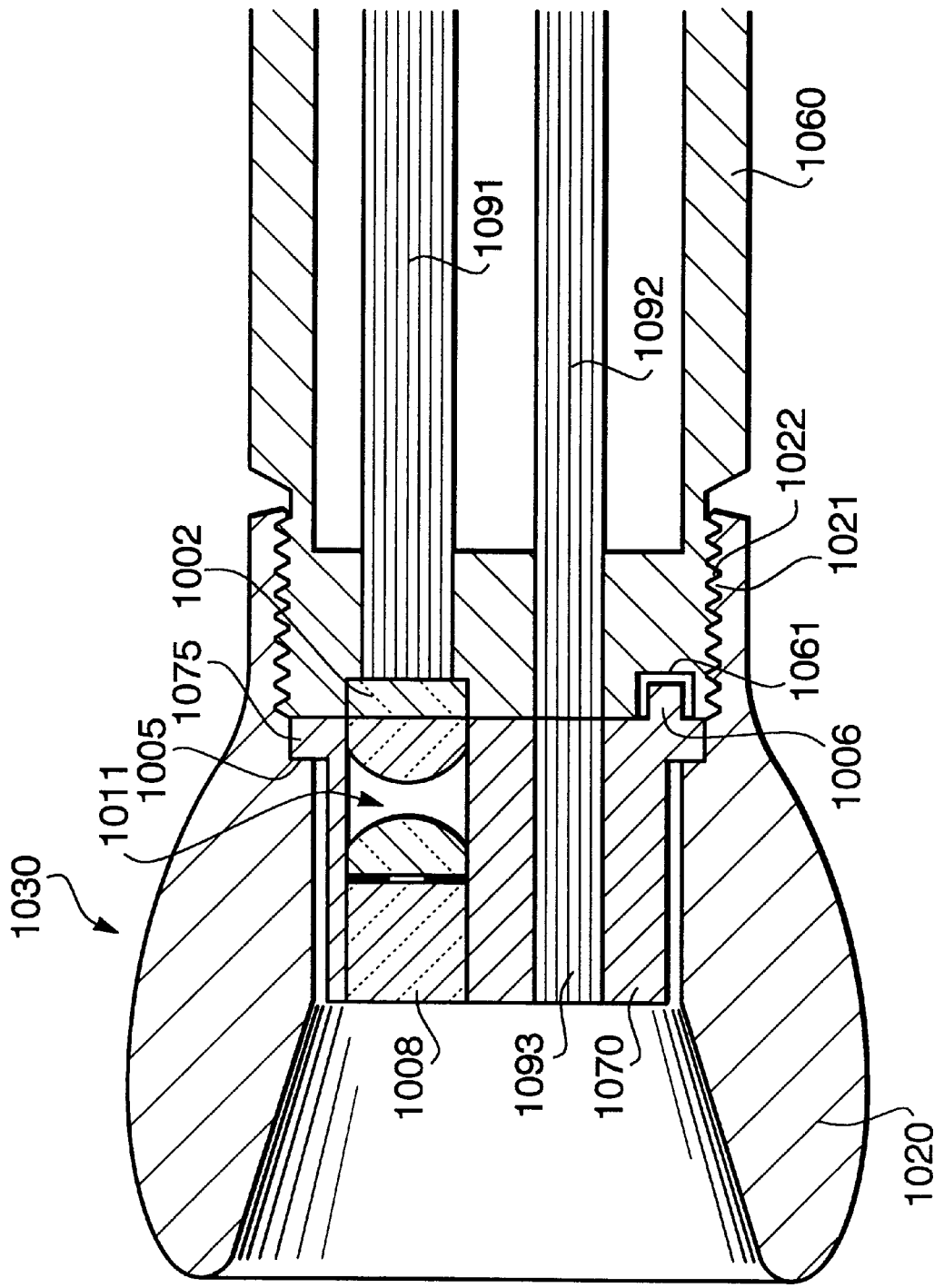
FIG. 31 is a sectional view of a detachable unit and a mounting portion of the tenth embodiment.

The tenth embodiment of the present invention is described. FIG. 31 is a sectional view of an adapter and a mounting portion of the tenth embodiment. An adapter 1030 includes a cylindrical adapter body 1070 and a hood 1020. The adapter body 1070 accommodates an object optical system 1011 for observing a human body cavity and a cover glass 1008 for covering the object optical system 1011. An image-fiber-bundle 1091 is provided to a mounting portion 1060 for carrying image formed by the object optical system 1011. The emit end of the image-fiber-bundle 1091 is covered by a cover glass 1002.

The hood 1002 has an internal thread 1021 at the inner surface thereof. The mounting portion 1060 has an external thread 1022 at the outer surface thereof. The hood 1020 is rotatable and slidable (in the direction of an axis of the adapter body 1070) on the adapter body 1070, so that the hood 1020 is fixed to the mounting portion 1060 by the engagement of the threads 1021 and 1022. In this state, the adapter body 1070 is urged by the shoulder portion 1005 against the mounting portion 1060. With this, the adapter 1030 is surely mounted in the mounting portion 1060. Further, the adapter 1030 can be removed by rotating the hood 1020 to loosen the engagement of threads 1021 and 1022.

An illumination-fiber-bundle 1092 is provided to the mounting portion 1060. The adapter body 1070 has an adapter-fiber-bundle 1093. The illumination-fiber-bundle 1092 and the adapter-fiber-bundle 1093 have mating surfaces aligned with each other. When the adapter body 1070 is mounted to the mounting portion 1060, the illumination-fiber-bundle 1092 and the adapter-fiber-bundle 1093 constitute a continuous fiber.

As constructed above, it is possible to replace the optical system (provided in the adapter 1030) only by removing the hood 1020 from the mounting portion 1060. Thus, the replacement of the optical system becomes easy. Further, since the hood 1020 is round-shaped, it is easy to insert the insertion tube in the human body cavity.

In this embodiment, the adapter 1030 can be replaced by side-viewing adapter 1130 as shown in FIG. 32. A side-viewing adapter 1130 has a prism 1108 (instead of the cover glass 1008) and an L-bent adapter fiber-bundle 1193. A hood 1120 of the side-viewing adapter 1130 has front, intermediate and rear portions 1121, 1122 and 1123. The front and rear portions 1121 and 1123 have larger diameter than the intermediate portion 1122. The intermediate portion 1122 has an opening 1110 corresponding to the prism 1108 and the exit end of the adapter-fiber-bundle 1193.

With such an adapter, it is possible to observe the side portion (with respect to the inserting direction of the insertion tube) of a human body cavity. Further, due to the front and rear portions 1121 and 1123, it is possible to urge a sticky surface of a human body cavity away from the adapter, thereby to keep an appropriate distance between the surface and the object optical system.

Although the structure and operation of a endoscope is described herein with respect to the preferred embodiments, many modifications and changes can be made without departing from the spirit and scope of the invention.

The present disclosure relates to subject matters contained in Japanese Patent Application Nos. HEI 09-34182, HEI 09-34183, HEI 09-34184, HEI 09-34185, HEI 09-34186, HEI 09-34187, and HEI 09-34188, filed on Feb. 19, 1997, which are expressly incorporated herein by reference in their entirety.

What is claimed is:

1. An endoscope, comprising:
   an insertion tube which can be inserted into a human body;
   an imaging device;
   an object optical system which forms an image on the imaging device;
   a detachable unit accommodating the imaging device and the object optical system and having a first surface;
   a mounting portion provided on a tip of the insertion tube, to which the detachable unit is detachably mounted, the mounting portion having a second surface which mates with the first surface of the detachable unit when the detachable unit is mounted;
   at least one first contact formed on the first surface of the detachable unit; and
   at least one second contact formed on the second surface of the mounting portion;
   wherein the first and second contacts are electrically connected when the detachable unit is mounted to the mounting portion;
   wherein the second surface is curved so that the second surface is elastically deformed when the detachable unit is mounted to the mounting portion, and
   wherein the second contact is urged against the first contact, ensuring the connection between the first and second contacts.

2. The endoscope according to claim 1, further comprising a waterproof arrangement which prevents water from entering into a connecting portion of said first and second contacts when said detachable unit is mounted to said mounting portion.

3. The endoscope according to claim 2, wherein said mounting portion has a waterproof structure, in a state said detachable unit is removed from said mounting portion.

4. The endoscope according to claim 2, wherein said detachable unit has a waterproof structure, in a state said detachable unit is removed from said mounting portion.

5. The endoscope according to claim 1, wherein said detachable unit further comprises an first engaging member, and
   wherein said mounting portion further comprises a second engaging member which engages said first engaging member.

6. The endoscope according to claim 5, wherein said first and second engaging members respectively comprise thread portions.

7. The endoscope according to claim 1, wherein said first and second engaging members respectively comprise end surfaces of said detachable unit and said mounting portion, said end surfaces mating with each other.

8. The endoscope according to claim 7, wherein a direction in which said detachable unit is mounted to said mounting portion is in parallel to a longitudinal axis of said detachable unit.

9. The endoscope according to claim 7, wherein said first contact comprises a plurality of contact elements, and said second contact comprises a plurality of contact elements.

10. The endoscope according to claim 7, wherein said first and second contacts mate with each other in a direction of a longitudinal axis of said detachable unit.

11. The endoscope according to claim 7, wherein one of said first and second contacts comprises a pin, and the other comprises a tube that receives said pin therein.

12. The endoscope according to claim 1, said detachable unit further comprising a first engaging member, said mounting portion further comprising a second engaging member,
   wherein said first and second engaging members constitute an bayonet mechanism.

13. The endoscope according to claim 1, said detachable unit comprising:
   a unit body accommodating said imaging device and said optical system; and
   a hood surrounding the unit body, the hood being slidable in a direction in which the detachable unit is mounted to the mounting portion,
   wherein said hood is slidable so as to engage said mounting portion.

14. The endoscope according to claim 1, further comprising:
   a fiber support pipe extending from the mounting portion, the fiber support pipe being provided to accommodate a fiber bundle for providing illumination light,
   wherein the detachable unit further has a hole that receives the fiber support pipe when the detachable unit is mounted to the mounting portion.

15. An endoscope, comprising:
   an insertion tube which can be inserted into a human body;
   an imaging device;
   an object optical system which forms an image on the imaging device;
   a mounting portion provided on a tip of the insertion tube and having a hole;
   a detachable unit accommodating the imaging device and the object optical system, the detachable unit being detachably mounted to the mounting portion;
   a protrusion that extends from the detachable unit and received by the hole of the mounting portion when the detachable unit is mounted to the mounting portion;
   at least one ring-shaped first contact surrounding the protrusion; and
   at least one second contact formed on an inner surface of the hole of the mounting portion,
   wherein the ring-shaped first contact and second contact are electrically connected when the detachable unit is mounted to the mounting portion.

16. The endoscope according to claim 15, said detachable unit comprising:
a unit body accommodating said imaging device and said optical system; and
a hood surrounding the unit body, the hood being slidable in a direction in which the detachable unit is mounted to the mounting portion,
wherein said hood is slidable so as to engage said mounting portion.

17. The endoscope according to claim 16, wherein said hood extends from a front of the unit body, the front being the direction in which said insertion tube is inserted into the human body.

18. The endoscope according to claim 17, wherein the hood has an arcuate shape in a length direction.

19. The endoscope according to claim 17, wherein the hood has an arcuate shape in a length direction.

20. The endoscope according to claim 15, further comprising a waterproof arrangement which prevents water from entering into a connecting portion of said first and second contacts, when said detachable unit is mounted to said mounting portion.

21. The endoscope according to claim 15, wherein said first contact comprises a plurality of contact elements, and said second contact comprises a plurality of contact elements.

22. The endoscope according to claim 21, wherein said plurality of contact elements are arranged along the direction of a longitudinal axis of said detachable unit.

23. The endoscope according to claim 15, wherein said detachable unit further comprises an first engaging member, and
wherein said mounting portion further comprises a second engaging member which engages said first engaging member.

24. The endoscope according to claim 23, wherein said first and second engaging members respectively comprise threads engaging with each other.

25. The endoscope according to claim 15, said mounting portion further comprising a first pipe in which a first fiber bundle is provided,
said detachable unit further comprising a second pipe in which a second fiber bundle is provided,
wherein said first and second pipes are aligned with each other when said detachable unit is mounted to said mounting portion, so that an illustration light is carried through said first and second fiber bundles.

26. An endoscope comprising:
an insertion tube which can be inserted into a human body;
an imaging device;
an object optical system which forms an image on the imaging device;
a detachable unit accommodating the imaging device and the object optical system, and having a hole;
a mounting portion provided on a tip of the insertion tube, to which the detachable unit is detachably mounted;
a fiber support pipe extending from the mounting portion and received by the hole of the detachable unit when the detachable unit is mounted to the mounting portion, the fiber support pipe accommodating a fiber bundle carrying illumination light;
at least one first contact provided on an inner surface of the hole of the detachable unit; and
at least one second contact formed on an outer surface of the fiber support pipe;
wherein the first and second contacts are electrically connected when the detachable unit is mounted to the mounting portion.

27. The endoscope according to claim 26, wherein said first contact comprises a plurality of contact elements, and said second contact comprises a plurality of contact elements.

28. The endoscope according to claim 26, wherein the fiber support pipe comprises a plurality of fiber support pipes, and the hole provided on the detachable unit comprises a plurality of holes.

29. The endoscope according to claim 26, said detachable unit comprising:
a unit body accommodating said imaging device and said optical system; and
a hood surrounding the unit body, the hood being slidable in a direction in which the detachable unit is mounted to the mounting portion,
wherein said hood is slidable so as to engage said mounting portion.

30. The endoscope according to claim 26, wherein the detachable unit has a second hole,
the endoscope further comprising a channel through which fluid can be fed, the channel extending from the mounting portion, the channel being inserted into the second hole when the detachable unit is mounted to the mounting portion;
at least one third contact provided on an inner surface of the second hole of the detachable unit; and
at least one fourth contact provided on an outer surface of the channel;
wherein the third and fourth contacts are electrically connected when the detachable unit is mounted to the mounting portion.

31. The endoscope according to claim 26, the detachable unit comprising:
a unit body accommodating the imaging device and the optical system; and
a hood surrounding the unit body, the hood being made of a plastic and having a hook;
wherein the mounting portion has a recess;
wherein the hood is deformable so that the hook engages the recess upon urging of the hood onto the mounting portion, when the detachable unit is mounted on the mounting portion.

32. An endoscope, comprising:
an insertion tube which can be inserted into a human body;
an imaging device;
an object optical system which forms an image on the imaging device;
a detachable unit accommodating the imaging device and the object optical system and having a hole along the central longitudinal axis of the detachable unit;
a mounting portion provided on a tip of the insertion tube, to which the detachable unit is detachably mounted;
a fiber support pipe extending from the mounting portion and aligned with the central longitudinal axis of the mounting portion, the fiber support pipe accommodating a fiber bundle for carrying illumination light and being inserted into the hole of the detachable unit when the detachable unit is mounted to the mounting portion;
at least one first contact provided to the detachable unit; and at least one second contact provided on the mounting portion, wherein the first and second contacts are electrically connect when the detachable unit is mounted to the mounting portion.

33. The endoscope according to claim 32, the detachable unit comprising:

a unit body accommodating the imaging device and the optical system; and a hood surrounding the unit body, the hood being slidable in a direction in which the detachable unit is mounted to the mounting portion, wherein the hood is slidable so as to engage the mounting portion.

34. The endoscope according to claim 32, wherein the at least one first contact is provided on an inner surface of the hole of the detachable unit, and the at least one second contact is provided on an outer surface of the fiber support pipe.

35. The endoscope according to claim 32, wherein the detachable unit has a recess that receives a front portion of the mounting portion, the front being a direction in which the insertion tube is inserted in the human body, the endoscope further comprising;

a first claw protruding outward from the front portion of the mounting portion; and a second claw protruding inward from an inner surface of the recess, wherein the first claw and the second claw are engaged by fitting the front portion of the mounting portion into the recess of the detachable unit and rotating the detachable unit, when the detachable portion is mounted to the mounting portion.

36. An endoscope, comprising:

an insertion tube which can be inserted into a human body;

an imaging device;

an object optical system which forms an image on the imaging device;

a mounting portion provided on a tip of the insertion tube and having a recess that has a first side wall extending in a direction in which the detachable unit is mounted to the mounting portion;

a detachable unit accommodating the imaging device and the object optical system and detachably mounted to the mounting portion, the detachable unit having a rear portion that has a second side wall extending in a direction in which the detachable unit is mounted to the mounting portion and is received by the recess when mounted;

at least one first contact formed on the outer surface of the second side wall of the rear portion; and at least one second contact formed on the inner surface of the first side wall of the recess;

wherein the first and second contacts are electrically connected when the detachable unit is mounted to the mounting portion.

37. The endoscope according to claim 36, wherein said recess comprises a cylindrical recess into which said rear portion of said detachable unit fits.

38. The endoscope according to claim 36, wherein said first contact comprises a plurality of contact elements, and said second contact comprises a plurality of contact elements.

39. The endoscope according to claim 38, further comprising a waterproof arrangement which prevents water from entering into a connecting portion of said first and second contacts when said detachable unit is mounted to said mounting portion.

40. The endoscope according to claim 36, the detachable unit comprising:

a unit body accommodating the imaging device and the optical system; and a hood surrounding the unit body, the hood being slidable in a direction in which the detachable unit is mounted to the mounting portion;

wherein the hood is slidable so as to engage said mounting portion.

41. The endoscope according to claim 36, further comprising:

a fiber support pipe extending from the mounting portion, wherein the detachable unit has a hole that receives the fiber support pipe when the detachable unit is mounted on the mounting portion.

* * * * *